United States Patent [19]
LaBerge et al.

[11] Patent Number: 5,507,716
[45] Date of Patent: Apr. 16, 1996

[54] EQUIPMENT AND METHODS USED TO INDUCE LUCID DREAMS IN SLEEPING PERSONS

[75] Inventors: Stephen P. LaBerge, Portola Valley; Robert S. Rich, Mountain View; David K. Wright, Soquel; Daniel G. Kottke, Palo Alto, all of Calif.

[73] Assignee: The Lucidity Institute, Inc., Palo Alto, Calif.

[21] Appl. No.: 748,193

[22] Filed: Aug. 21, 1991

[51] Int. Cl.$^6$ ............................................. A61M 21/00
[52] U.S. Cl. .................................................... 600/27
[58] Field of Search ............... 600/26–28; 128/897–898

[56] References Cited

U.S. PATENT DOCUMENTS

| | | | |
|---|---|---|---|
| 4,858,609 | 8/1989 | Cole | 600/26 |
| 4,902,274 | 2/1990 | Gleeson, III | 600/27 |
| 5,101,831 | 4/1992 | Koyama et al. | 600/26 |

*Primary Examiner*—Angela D. Sykes
*Assistant Examiner*—J. P. Lacyk

[57] ABSTRACT

Equipment and methods employed to assist people to achieve lucid dreams (dreams in which one is aware that one is dreaming) function by detecting and monitoring the eye and head movements of sleeping persons for the presence of sufficient eye movement activity in the absence of head movement to indicate the presence of REM sleep and then applying sensory stimuli to sleepers in REM sleep, which if incorporated into their dreams, can cue them that they are dreaming without producing awakening. With this equipment and methods, people are able to have more lucid dreams than they otherwise would. A preferred embodiment includes a face mask that contains two infrared emitter-detector pairs, one for sensing eye movements and one for sensing body movements, a state-test button, and components that produce low intensity sensory stimuli such as light and sound. A microprocessor monitors the fluctuating voltage from the infrared pairs for the occurrence of a predetermined sequence of voltages, adjustable in software, and when the correct sequence occurs, triggers the stimuli-producing components in the mask into activity, to cue the sleeper to become lucid. The methods include many procedures and adjustable parameters for optimizing the timing of the application of the sensory cues to the sleeper. Among these procedures and parameters are those used to locate the time in the sleeper's REM periods when the cue will be most effective, and those used to apply the sensory stimuli at these optimal times.

40 Claims, 22 Drawing Sheets

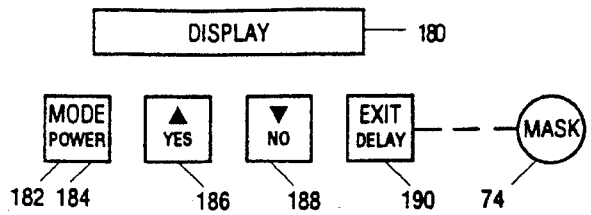

MODE DISPLAYS AND FUNCTIONS
The following is a list of the modes for setting and using the Dreamlight. They are listed in the order in which they appear when the MODE button is pressed repeatedly.

Pressing the MODE button turns the DreamLight on.

MODE 1: WELCOME DREAMER
YES enters DREAM MONITORING (MODE 13).
MODE enters edit modes.
EXIT quits and turns the DreamLight off.

MODE 2: CUE LENGTH
Determines how long the light flashes with each cue.

▲ increases the length of the light cue.
▼ decreases the length of the light cue.
MODE continues to MODE 3.
EXIT returns to MODE 1.

MODE 3: BRIGHTNESS
Sets the brightness level of the light cue.

▲ increases the brightness of the light cue.
▼ decreases the brightness of the light cue.
MODE continues to MODE 4.
EXIT returns to MODE 1.

MODE 4: FLASHES
Provides a choice of several flash styles.

▲ or ▼ cycles through the options OFF, REGULAR, RANDOM, RAMPUP, and RAMPDOWN.
MODE continues to MODE 5.
EXIT returns to MODE 1.

MODE 5: [NIGHT RECORDS, e.g. 0126M458 S05C013]
Selects and displays information from the last 10 nights the DreamLight has recorded. The screen shows 4 numbers, the time the DreamLight was turned on, the length of the record in minutes, the sensitivity level used, and the number of cues given during the record. The example above shows the start time as 01:26, the record length as 458 minutes, the sensitivity setting as 5, and the number of cues given as 13.

▲ cycles through the stored data records.
MODE continues to MODE 6.
EXIT returns to MODE 1.

MODE 6: #CUES DESIRED
Enter here the number of cues desired for the night selected in NIGHT RECORDS. The next mode determines the sensitivity that would give the right number of cues.

▲ increases the number of cues desired.
▼ decreases the number of cues desired.
MODE continues to MODE 7.
EXIT returns to MODE 1.

MODE 7: SENSITIVITY CHK?
Calculates the number of cues at each sensitivity level beginning with 1 and moving upwards until the number of cues is greater or equal to the number requested in MODE 6. The result is then displayed: "IF S=X, CUES=Y."

YES begins calculation.
MODE continues to MODE 8.
EXIT returns to MODE 1.

MODE 8: SENSITIVITY
Sets the DreamLight's sensitivity to eye movements.

▲ increases the sensitivity setting.
▼ decreases the sensitivity setting.
MODE continues to MODE 9.
EXIT returns to MODE 1.

MODE 9: DREAMALARM®
Causes the speaker in the mask to beep 3 minutes after each light cue, awakening the user and aiding dream recall.

▲ or ▼ cycles through the options OFF, SOFT, LOUD.
MODE continues to MODE 10.
EXIT returns to MODE 1.

MODE 10: WAKEUP
Causes the speaker in the mask to beep, awakening the user at the time set. Any key press turns off the alarm.

▲ or ▼ turns the WAKEUP alarm ON or OFF.
MODE continues to MODE 11.
EXIT returns to MODE 1.

MODE 11: WAKEUP HOUR
Sets the hour that the WAKEUP alarm sounds.

▲ or ▼ to turn the WAKEUP alarm ON or OFF.
MODE continues to MODE 12.
EXIT returns to MODE 1.

MODE 12: WAKEUP MIN
Sets the minute that the WAKEUP alarm sounds.

▲ or ▼ to turn the WAKEUP alarm ON or OFF.
MODE or EXIT returns to MODE 1.

MODE 13: [DREAM MONITORING e.g. 23:20 C01 D014 Z]
Monitors sleep and delivers cues when the user is dreaming. The display shows the current time, the number of cues given so far, the amount of time left in the delay, and a blinking Z. In the example above, the time is 23:20, 1 light cue has been given, and there are 14 minutes left in the delay. While the delay is counting down, no cues will be given, allowing the user to fall asleep undisturbed.

DELAY adds 10 minutes to the delay time
NO resets the delay to 0.
MODE and EXIT exits MODE 13.

FIG. 11

EQUIPMENT AND METHODS USED TO INDUCE LUCID DREAMS IN SLEEPING PERSONS

BACKGROUND

As set forth in the book entitled *Exploring the World of Lucid Dreaming*, written by Stephen LaBerge and Howard Rheingold, the idea of cultivating a state of mind while awake for the purpose of carrying it into a dream state as a means of inducing lucid dreams, has been used by Tibetan Buddhists for more than a thousand years. However as recently as the late 1970's, experts were convinced that dreaming with consciousness that you were dreaming was a contradiction in terms and therefore impossible. At this recent time Stephen LaBerge began his Ph.D. studies of lucid dreams at Stanford University to establish proof that lucid dreaming was real, by obtaining evidence from the dream world that a person knew he or she was dreaming during sleep.

During his studies, he, with the assistance of other persons, has developed experimental testing equipment for helping him and other persons to obtain such evidence from the dream world. In so doing, the developed experimental testing equipment, in many embodiments, has also been designed and built to help persons who are lucid dreamers, or wish to try to become lucid dreamers, to have lucid dreams and to have them more often and to have them more effectively. These lucid dreamers are referred to as being Oneironauts.

Also other persons have developed equipment, such as Keith M. T. Hearne who illustrated and described his respiratory measuring device in his U.S. Pat. No. 4,420,001 of 1983. His device sensed temperature changes of a person's respiration in his or her breathing passageway, or in airflows to and from his or her breathing passageway. Thermistors were used, in an electrical circuit, to sense the temperature changes of the person's respiration. When the rate of these temperature changes reached a high predetermined level, the signals created in the electrical circuit initiated an audible sound, either to help arouse a sleeping person from an unpleasant dream by awaking them or to help them enter into a lucid dream state.

At this time, a number of different techniques have been used to monitor sleep, in both the quiet phase and active phase, the latter also being called the rapid eye movement phase of sleep and referred to as REM sleep. These techniques include applications of: electrodes for EEG, ECG and EMG; infra-red sensing; and respiration measurement with strain-gauges or thermistors. Among these techniques, Stephen LaBerge and those helping him sought a method to reliably sense the presence of REM sleep, so that a device could automatically signal to a sleeper that he or she is dreaming. The requirements for such a device were portability, ease of use, low cost, and above all reliability and the successful induction of lucid dreams, which are those dreams wherein one is aware that one is dreaming.

SUMMARY

Stephen LaBerge and those helping him created better methods to help persons lucidly dream, and, in so doing, he and those helping him developed various embodiments of experimental test equipment that is used to make sleeping persons aware they are in the active phase of their sleep, and they are having a dream, while they still continue to dream or become lucid, and such equipment senses eye movements. They selected sensing movements of a person's eyes, via movement of his or her eyelids, because by using eye movement sensing, especially when combined with body movement sensing, and thereafter accounting for such body movements, to thereby ascertain accurately eye movements, per se, they developed very reliable test equipment for detecting the phases of sleep, and especially the active phase of sleep, called the rapid eye movement phase, which is further conveniently referred to as being REM sleep.

Their development of their methods and the experimental test equipment centering on eye movement sensing, undertaken by sensing eyelid movements, which so indicate eye movements, extended over a considerable period of time. Now equipment is soon to be made available for many persons to use in practicing their methods. In respect to a preferred embodiment of the equipment each person, during his or her sleep, is provided with a comfortably worn face mask covering face portions, and a headband supports the face mask about the person's head. The face mask, in turn, supports components of this equipment, which sense a person's eyelid movements during sleep, and which, then at the proper time, signals the person that he or she is dreaming, and thus should be able to be lucidly dreaming. The signal, preferably a light signal, occurs without awaking the person. Also a sound signal is selectively and optionally used.

The sensing components supported on the face mask utilize a low level infrared emitter positioned on the face mask to direct infrared light to the eyelid of a sleeping person, and a low level infrared detector to receive the reflections of this infrared light from the surface of this eyelid of this sleeping person. The signalling components supported on the face mask preferably utilize small flashable lights and/or small speakers to signal the sleeping person that he or she is dreaming, and thus should be able to be lucidly dreaming, without awaking the person.

A like arrangement of a low level infrared emitter, also positioned and supported on the face mask, but over a part of a person's face, which does not necessarily move with a person's eyelids, is also used with a low level infrared detector also positioned and supported on the mask, to detect face, head, or body movements, which are independent of a person's eyelid movements. These body movements are accounted for to avoid erroneous conclusions as to the eyelid movements, per se, and thereby to accurately determine whether or not a person is dreaming, or could be lucidly dreaming.

The other components of this preferred embodiment of the equipment are arranged together as a shelf or table supported subassembly, with circuitry extending to the sensing and signalling components supported and positioned on the face mask, These other components include:

analog signal conditioning group of components, in turn including alternating current coupling, a preamplifier, a low pass filter, a computer gain setting unit, and an integrating unit to receive signals from the infrared detector detecting eyelid movements;

an analog-digital converter for converting the analog signals of the eyelid movements into digital signals;

analog signal conditioning group of components, in turn including an alternating current coupling, a preamplifier, a low pass filter, a computer gain setting unit, and an integrating unit to receive signals from another infrared detector, detecting face, head, and/or body movements;

an analog-digital converter for converting the analog signals of the face, head, and/or body movements into digital signals;

a computer to receive the digital signal information from both the analog-digital converters, to receive signals via software instructions, to direct data to data storage, to direct signals to activate sensing lights, and to activate sensing speaker sounds.

DESCRIPTION OF THE DRAWINGS

The equipment used to make sleeping persons aware they are dreaming, while they still continue to dream, is illustrated in the drawings, in respective embodiments in which:

FIG. 9N illustrates circuitry, which is designated as the sound circuitry;

FIG. 11, in reference to the preferred embodiment, illustrates respectively, what visual displays and operating keys are observed, and when the latter are to be actuated, in respect to the equipment of the preferred embodiment, as shown in FIG. 1, which includes the computer components, inclusive of all the preferred circuitry, as shown in other figures.

DESCRIPTION OF THE PREFERRED EMBODIMENTS OF THE EQUIPMENT AND METHODS

Figure 1:
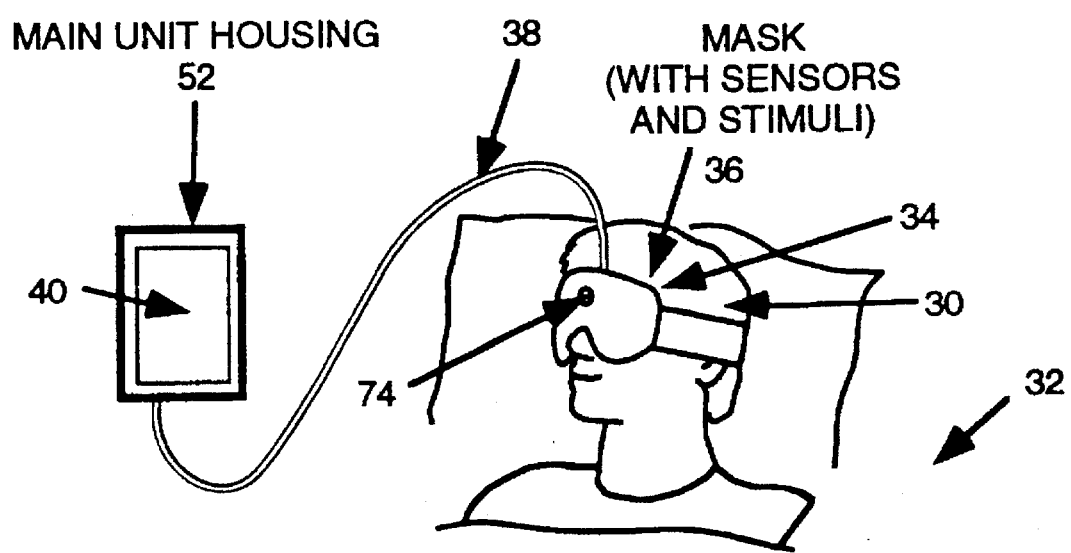
FIG. 1 is a top view of a preferred embodiment, looking down on a person sleeping in a bed, and nearby an assembly rests of many of the components of this equipment, except for electrical circuit wires extending to a face mask supported on the person's head, in turn positioning and supporting the other assembly of components of this testing equipment.

Quite recently, studies were undertaken, and they are continuing, to establish proof that lucid dreaming was and is real. Evidence was obtained and is being obtained, from what is called the dream world, that persons would know, and know, that they were and are dreaming during their sleep. Previously, for a very long time, many persons had realized that lucid dreaming had and has improved the quality of their waking life.

To better understand lucid dreaming, the overall aspects of sleeping, dreaming, and lucid dreaming are described. Sleep is not a uniform state of passive withdrawal from the world. There are two distinct kinds of sleep: a quite phase and an active phase, which are distinguished by many differences in biochemistry, physiology, psychology, and behavior. Changes in brain waves, as determined by the measurement at the scalp of electrical energy, eye movements, and muscle tone are used to determine these two phases, quiet or active.

The active phase of sleep is also called the rapid eye movement phase of sleep, also referred to as REM sleep. During REM sleep a person's eyes, under their closed lids, move rapidly about, much as they do when a person is awake. When their eyes move rapidly, their eyelids flutter.

A person's body, during this REM sleep, remains almost completely still, for the body is temporarily paralyzed to prevent a person from acting out her or his dream.

The quiet phase of sleep is divided into three substages: Stage one is a transitional state between drowsy wakefulness and light sleep, characterized by slow drifting eye movements, and vivid brief dreamlets called hypnagogic imagery, meaning leading into sleep. This stage one occurs only for a short time, as the sleeping person quickly passes through stage one;

Stage two is bona fide sleep, lasting only twenty to thirty minutes. The mental activity is sparse, mundane, and thought-like; and Stage three is delta sleep, lasting thirty to forty minutes, when brain waves are regular, large, and slow. There is very little dream content.

After stage three, a person returns to stage two for thirty to forty minutes. Then after these seventy to ninety minutes in this quiet phase of sleep, the sleeping person enters the active phase of sleep, i.e. REM sleep, for the first time each night. This active REM sleep lasts for five to ten minutes.

Possibly, following a brief awakening, in which a person may likely remember a dream, or without such awakening, a person sinks back into stage two of the quiet phase of sleep. Then a person possibly reenters stage 3, delta sleep. Then after ninety minutes a person returns again to active REM sleep. This overall sleeping cycle repeats during the night.

During a person's night of sleeping the duration of his or her periods of REM sleep will tend to increase with each cycle. Also the intervals, between these recycling REM sleep periods, decrease in time, from ninety to thirty minutes during the passing of the nighttime. Often, during a nighttime, involving five or six periods of dreaming, a person will awaken ten or fifteen times.

It is known that events, experienced by a person who is asleep and dreaming, produce effects on the person's brain, and to a lesser extent on the person's body, much the same, as if the person were to experience the corresponding events, while he or she was awake. Therefore, by learning to have lucid dreams, a person opens for himself or herself a better life full of all the delights he or she can imagine.

Lucid dreaming is used to rehearse for anything in life. Lucid dreaming, as suggested by some research, may prove to be an ideal training ground, to help athletes cultivate peak performance, and to help other persons, also, in developing their non athletic skills. Lucid dreaming is said to be useful in rehearsing anything in life.

In the lucid dreaming state, a person's conscious and unconscious minds meet face to face. The lucid dreams permit a person's deliberate access to a wide storage of knowledge. These lucid dreams, themselves, are conducive to the creativity of the person.

For those persons troubled by nightmares, lucid dreaming gives such persons the power to banish the terror in their nightmares, and at the same time to strengthen their courage. A person masters his or her fear sufficiently to recognize his or her most disturbing images, occurring during a nightmare, are his or her own creations, and therefore he or she is able to face these disturbing images. Lucid dreaming has a significant value in helping persons, especially children, discover that their fear has no more power than they let their fear have, and that they are the master of their fears.

Lucid dreaming may lead to better health. In lucid dreams persons may have an unparalleled opportunity for developing a high degree of self control of their bodies, which may prove useful in their self healing.

A person can use lucid dreams to plumb the depths of his or her identity and explore the frontiers of his or her inner world. Lucid dreams have been said to be and are a reservoir of knowledge and experience, which are often overlooked as a vehicle for exploring reality.

Therefore Embodiments of This Equipment Are Provided to Help Persons Have Lucid Dreams Because lucid dreaming may be so beneficial to a person's good health and other qualities of his or her life, and if his or her ability to lucidly dream may be enhanced, then steps to do so should be undertaken and are being undertaken. Such steps include providing training by oral and written presentations, in turn leading to acquiring routines and habits. Also now, such steps include providing equipment, such as the equipment illustrated and described herein, which, when used properly, assists a sleeping person to realize he or she is dreaming, or should be able to have a lucid dream. This equipment accurately records eye movements to determine when rapid eye movement sleep, called REM sleep, is occurring, and then applies stimuli, as a cue to the sleeping person to help her or him initiate or continue dreaming lucidly. The stimuli preferably is a blinking light, because light generally does not awaken a person. The stimuli also may be auditory created, for example by using a speaker to produce sounds. Moreover, both light and auditory stimuli may be used together. The stimuli must be strong enough to be perceivable by the sleeping person, during his or her REM sleep, but not be so strong as to awaken him or her. The stimuli should be incorporated into a person's dream in a clear and recognizable way.

This equipment, in determining the eye movements by observing the eyelid movements, also must distinguish other body movements, if they are occurring at the same time, so that eye movements, per se, will be determined. The equipment must be conveniently used, be portable, and be easily cared for by all persons, and especially by a person seeking to lucidly dream.

Figure 6:
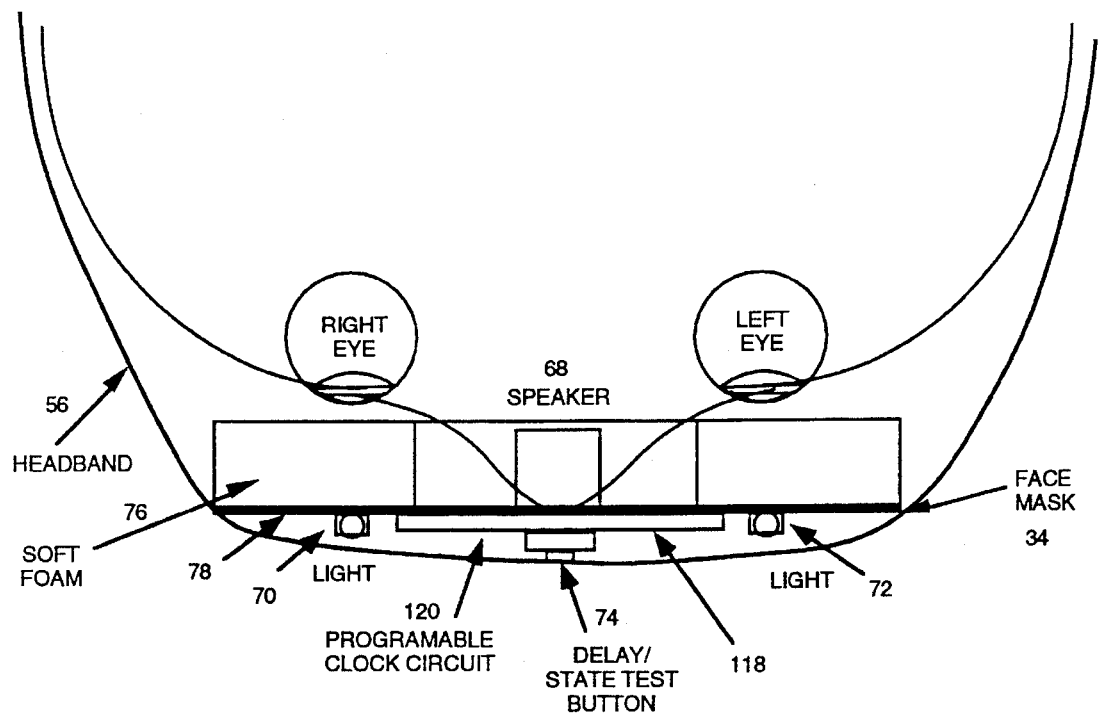
FIG. 6 is a view which is somewhat similar to FIG. 3, but another embodiment is shown which has fewer components, and this view is also a schematic top view of a face mask, indicating the relative positioning of this face mask, having fewer components, with the eyes and eyelids of the person, while he or she will be sleeping.
Figure 7:
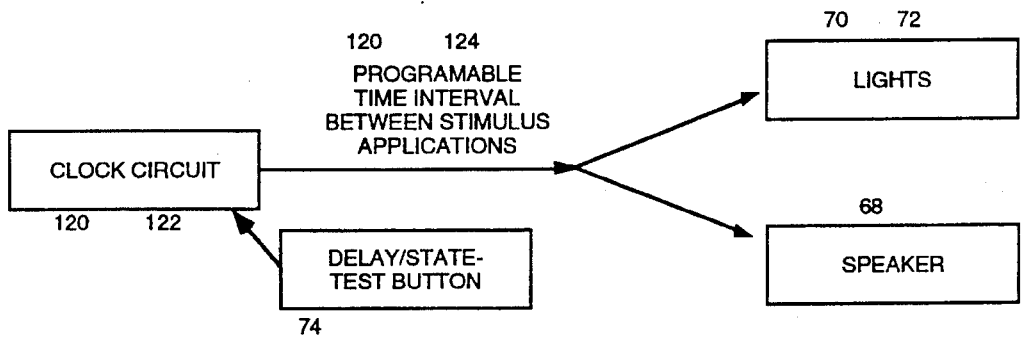
FIG. 7 is a block diagram indicating how a programmable clock circuit is used and supported in the face mask of the embodiment, illustrated in FIG. 6, to initiate the stimuli, either as light or sound cues, with the sound cues coming from a speaker.

The Preferred Embodiments of This Equipment Used to Help Persons Have Lucid Dreams Have Selectable Variable Numbers of Components To gain all the advantages of lucid dreaming, a preferred embodiment of this equipment, as illustrated in all the figures of the drawings, except essentially in FIGS. 6 and 7, pertaining to another embodiment, is operated both by a person seeking to lucidly dream, and/or with the help of assisting persons. A person may also operate equipment generally by himself or herself, in specific reference to the embodiment illustrated in FIGS. 6 and 7, to also gain the advantages of lucid dreaming.

The equipment, as shown in FIGS. 6 and 7, has fewer components, thereby providing lucid dreaming equipment at a lower cost. The equipment, as shown in all other figures, is representative of embodiments having additional components that are used to assist persons in determining the best ways for them to use this equipment, so they may enter a lucid dream, and/or continue their lucid dream. Also the equipment with more components, as illustrated in most of the figures, has these additional components, which are conveniently used by other assisting persons, who are, for example, researchers, and/or doctors, to in turn help persons who are trying to have lucid dreams, or who are having lucid dreams, to experience them to the fullest beneficial extent possible, and to record research data for subsequent studies.

Preferred Embodiment of the Equipment Having Many Components to Help Persons Have Lucid Dreams, and Have Other Persons be Able to Help Them by Also Using the Equipment FIG. 1 shows a person in bed 32, using the equipment 30, wearing a face mask 34 having an assembly of components 36 including a delay/state-test button 74, positioned and supported on the face mask 34. This assembly of components 36 is connected, via a flexible multi-conductor electrical cable 38, to an assembly of components 40, all arranged within a main unit housing 52.

Figure 2:
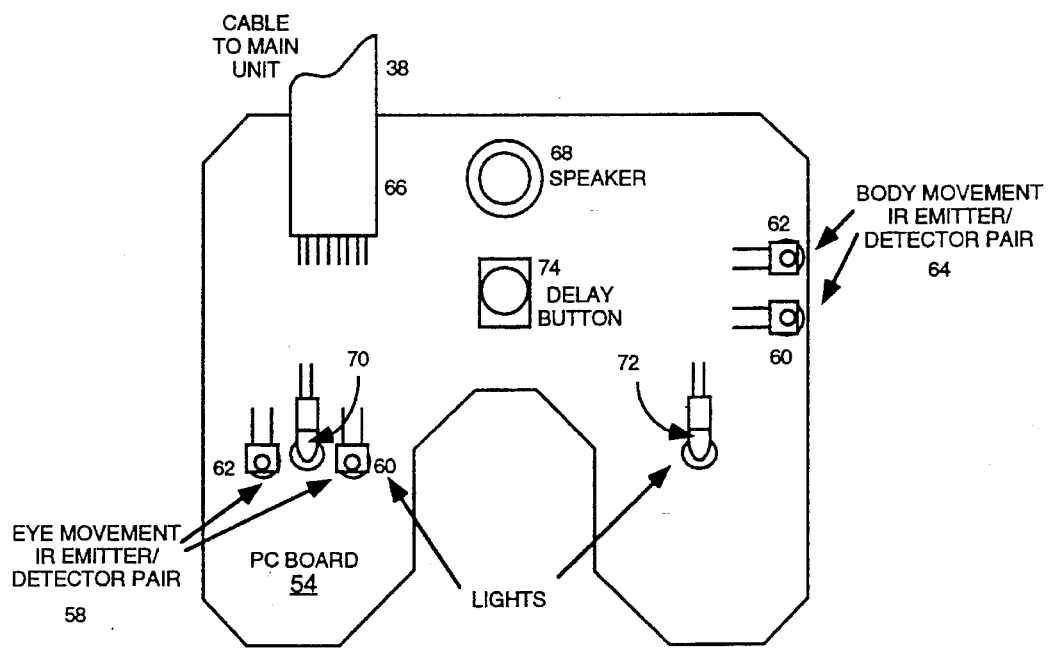
FIG. 2 is a schematic elevational view of a face mask to be worn by a person, while he or she is sleeping, as shown in FIG. 1, and used to position and to hold in place some of the components of this preferred embodiment of this equipment, such as: the commencing portions of electrical circuit wires arranged within a cable and to be interconnected with electrical circuit wires of the assembly of other components positioned and supported on the table nearby the bed; a printed circuit board; a speaker, a delay/state-test button; a paired infrared emitter and an infrared detector to detect rapid movement of a sleeping person's eyelids; and another paired infrared emitter and an infrared detector to detect the sleeping person's facial or body movements, independently of the detection of the movement of their eyelids, to thereby obtain movement information correctly indicating eyelid movements, per se, independently of body movements.
Figure 3:
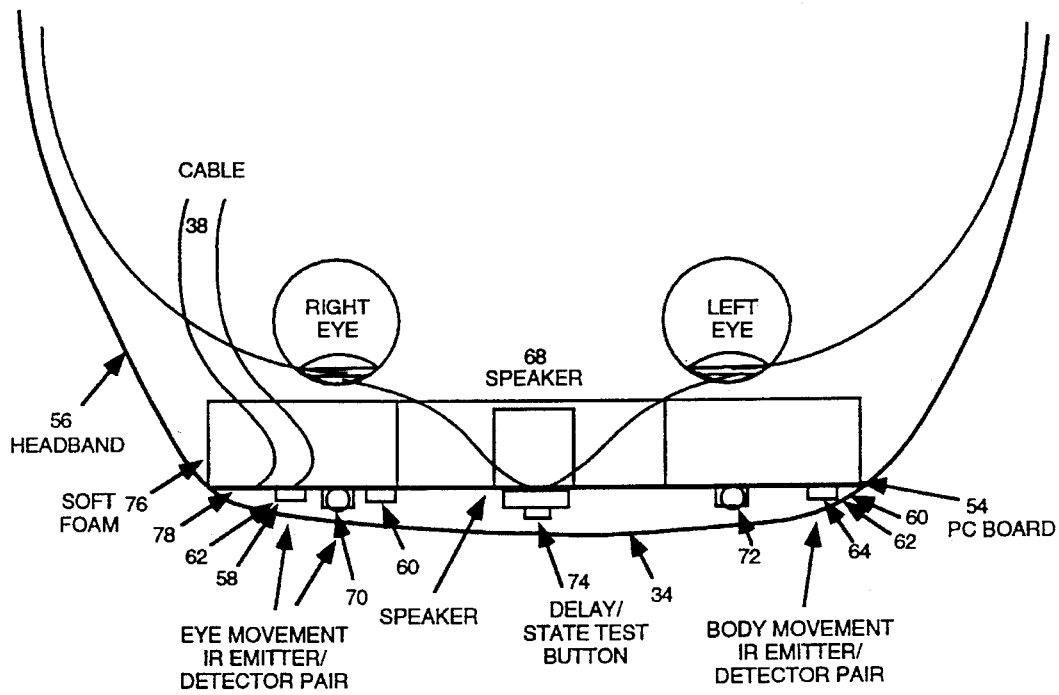
FIG. 3 is a schematic top view of the face mask, shown in FIGS. 1 and 2, again illustrating some of the components of this equipment, and also indicating the relative positioning of this face mask with the eyes and eyelids of the person, while he or she will be sleeping.

The assembly of components 36 and the face mask 34, supporting them, are schematically illustrated in FIGS. 2 and 3. The printed circuit board 54, also referred to as the PC board 54, of this assembly 36, is secured to the face mask 34. The headband 56 positions and supports the face mask 34, on the head of the sleeper, who is trying to have a lucid dream, or who is having a lucid dream.

The PC board 54, in turn positions and supports one pair 58 of an infrared emitter 60 and an infrared detector 62, also referred to as an IR emitter 60 and an IR detector 62, which are positioned, as a pair 58, over a person's right eyelid and right eye, who is using this equipment 30 to have a lucid dream. Also the PC board 54 positions and supports another pair 64 of an IR emitter 60 and an IR detector 62, over a person's left outer can thus, which is the face or head area located between the eyebrow and temple of a person who is using this equipment 30 to have a lucid dream.

This PC board 54, as shown in FIGS. 2 and 3, also positions and supports: an end 66 of the flexible multiple conductor cable 38; a speaker 68 to produce a sound as a stimulus, in turn serving as a cue to the dreaming person that she or he is dreaming; two lights 70, 72 to produce light as a stimulus, in turn serving as a cue to the dreaming person that she or he is dreaming; a delay/state-test button 74 operable to delay the operation of the stimuli until after a person has entered a lucid dream and also to function as a convenient state-test to allow persons to discover that they are dreaming that they have awakened if such is the case (if the lights fail to flash upon button press the user has probably only dream that the button has been pressed and is therefore dreaming); and a soft plastic foam pad 76 fitted over portions of a person's face as he or she is sleeping, and soon will be or is lucidly dreaming.

Figure 4:
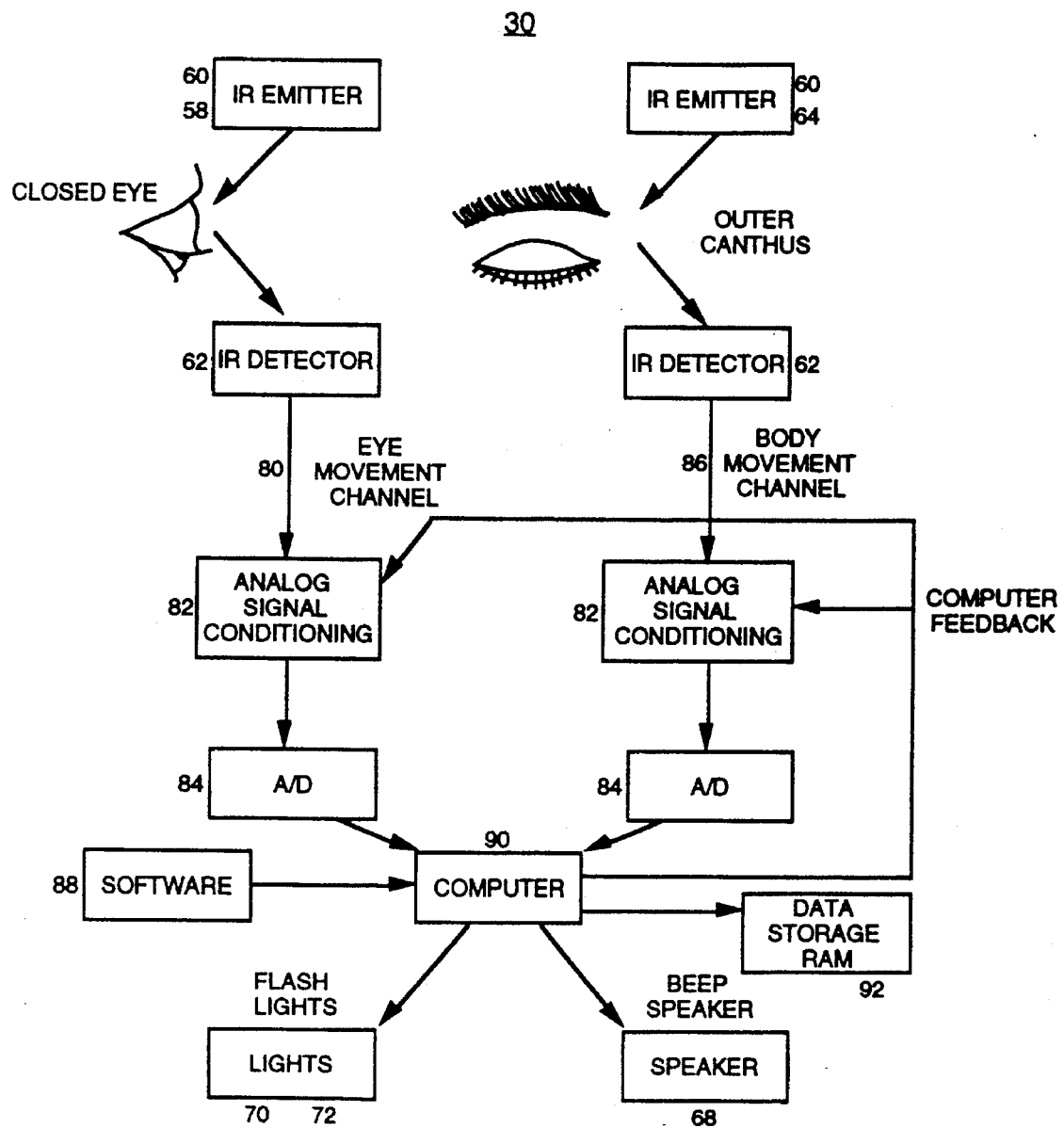
FIG. 4 is a block diagram indicating a preferred general arrangement and functioning of this preferred embodiment of this equipment.

Block Diagrams Are Used to Help Explain How the Equipment, Having Many Components, is Utilized by a Person Hoping to Have or is Having a Lucid Dream, and by Persons Helping This Person to Have a Lucid Dream and/or to Continue Her or His Lucid Dreaming How the equipment 30 is to be implemented is depicted in the general block diagram of FIG. 4. An IR emitter 60 focuses a dim cone of IR light on the closed eyelid of the person who is sleeping, and who wants to use this equipment 30 to help him or her with his or her efforts to lucidly dream. Movements of the person's eye cause the eyelid to flutter, which alters the intensity of the IR light reflected back to the IR detector 62. This IR detector 62 then converts these fluctuations in light energy into changes of voltage in electrical energy, which, via the eye movement channel 80, are then filtered and amplified by analog signal conditioning circuitry 82. The resulting electrical energy signal is digitized by using an analog to digital converter 84, noted by A/D in FIG. 4.

Other movements of other body portions of a person who is sleeping and who wants to use the equipment 30 to help him or her with his or her lucid dreaming, are also detected and accounted for. Thereby, eye movements, per se, detected by observing eyelid movements, will be specifically observed to more accurately determine when a person is in REM sleep.

These other body movements are detected by a similar process, as that process which is used to detect eyelid movements. Another pair 64, of an IR emitter 60 and an IR detector 62, is used. An IR emitter 60 is directed toward the outer can thus of the person, which is a facial portion which is effected very little, if at all, by eye movements. This outer can thus is very sensitive to movements of the face mask 34. When the person sleeping moves, the position of the face mask 34 shifts slightly.

The movements of the outer can thus cause light energy changes, thereby creating signals indicating a person's body movements. These body movement signals are picked up by the IR detector 62 of this another pair 64 of the IR emitter 60 and IR detector 62. These body movement signals, via the body movement channel 86, reach another analog signal conditioning circuitry 82. The resulting electrical energy signals are digitized by using another analog to digital converter 84, noted by A/D in FIG. 4.

These respective digitized signals of electrical energy respectively representing eyelid movements and body movements of a person sleeping in a REM sleep period, as shown in FIG. 4, via instructions of software 88 enter a computer 90. In this computer 90, these respective electrical energy signals of eyelid movements and body movements are monitored. The computer 90 directs some of these signals to a data storage 92, also referred to as RAM memory 92, for later review and examination.

The computer 90 also evaluates these signals of eye and body movements to detect the oncoming presence and continuance of the sleeping person's REM sleep. Then the computer 90, via the software 88, is programmed to blink or to flash the lights 70, 72, positioned and supported on the face mask 34, and/or to activate the speaker 68, positioned and supported on the face mask 34, to create the stimuli to cue the person who is in REM sleep that he or she is dreaming, or may soon be lucidly dreaming.

Figure 5:
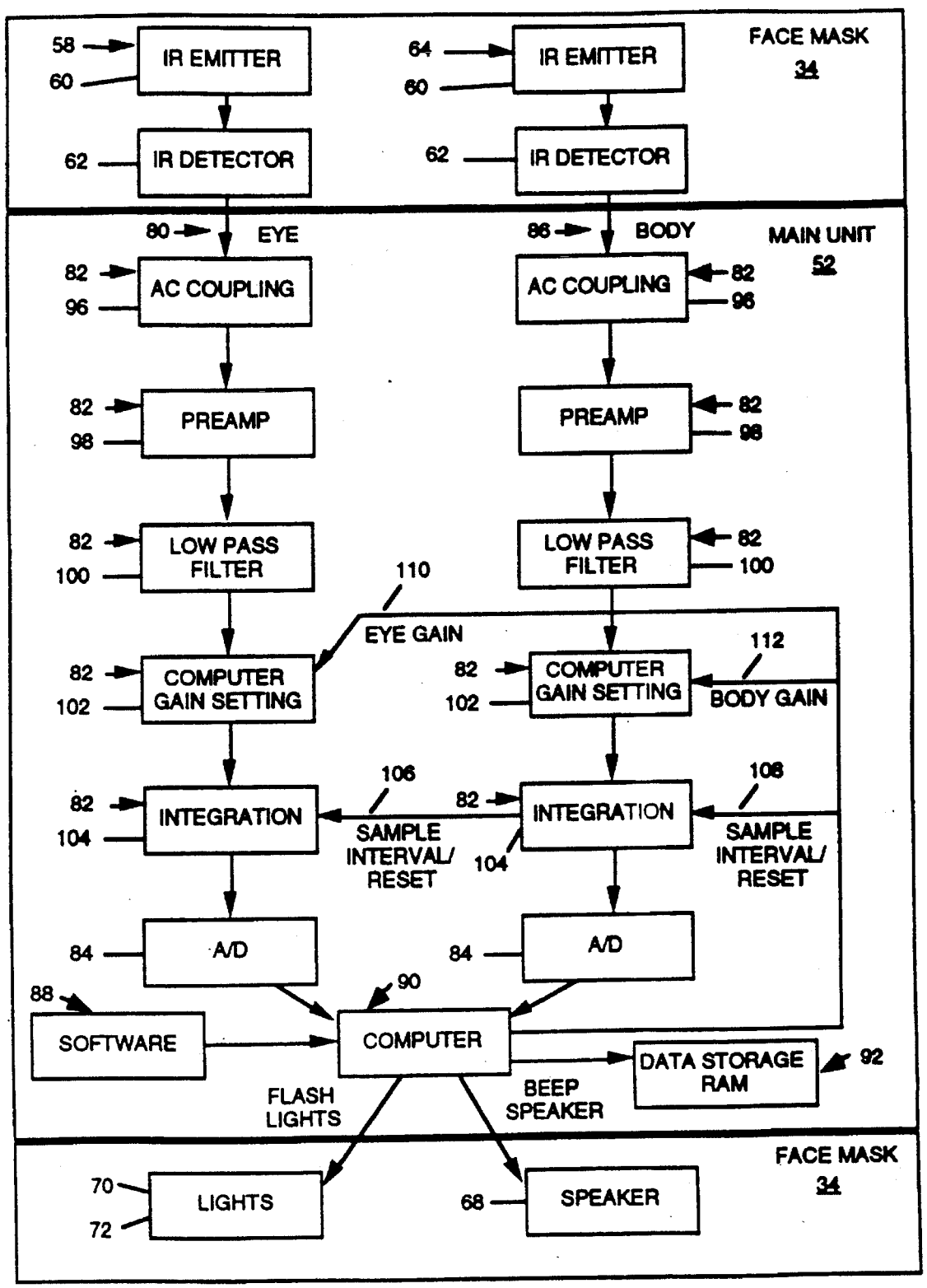
FIG. 5 is another block diagram further indicating more of the specific components of a preferred general arrangement and functioning of this preferred embodiment of this equipment, and also by using boundary lines to designate which specific components, as an assembly, are supported on the face mask, and which specific components are supported as an assembly on the table as shown in FIG. 1.

The general block diagram of FIG. 4 is supplemented by the expanded detailed block diagram of FIG. 5. What the analog signal conditioning circuitry 82, preferably comprises, is shown as being the arrangement, in both the eye movement channel 80 and the body movement channel 86, of: an alternating current coupling 96, also referred to as the AC coupling 96; a preamplifier 98, also referred to as a preamp 98; a low pass filter 100; a computer gain setting unit 102; an integration unit 104, which receives a respective sample interval reset signal, with one such signal 106 for the eye movement channel 80, and signal 108 for the body movement channel 86, both of these signals coming from the computer 90. Each computer gain setting unit 102 receives a respective gain signal, with one such signal 110 for the eye movement channel 80, and signal 112 for the body movement channel 86, both of these signals coming from computer 90. The other blocks of this FIG. 5, remain as described and illustrated in respect to the block diagram of FIG. 4.

The three rectangular boundary blocks in FIG. 5, respectively indicate the face mask 34 positioning and supporting portions for one assembly of components, and the main unit 52 positioning and supporting portions for the other assembly of components, of this preferred embodiment 30. This preferred equipment 30, has many components to be utilized by the person desiring to lucidly dream, or having a lucid dream, and also to be utilized by a person or persons helping this sleeping person trying to lucidly dream or having his or her lucid dream.

Another Embodiment of the Equipment Having Fewer Components to Help a Person Have a Lucid Dream To help persons wanting to learn to have lucid dreams, to learn to have more lucid dreams, or to have longer lucid dreams, and who prefer to use equipment which is less complex and lower in cost, another embodiment is available, as illustrated schematically in FIGS. 6 and 7. The face mask 34 and head band 56, as shown in FIG. 6, support only: lights 70, 72, and speaker 68 to ultimately provide the stimuli to cue the sleeping person that he or she is lucidly dreaming, or could be lucid dreaming; a circuit board 118 having a programable clock circuit 120; a delay/state-test button 74 operable to delay the operation of the stimuli until after a person has entered a lucid dream and also to provide a convenient state-test (if the lights fail to flash upon button press the user has probably only dream that the button has been pressed and is therefore dreaming); and a self contained electrical energy source, not shown, or an electrical conductor cable portion 38 connected to an electrical energy source, as shown in FIG. 2.

The block diagram of FIG. 7, illustrates the functional arrangement of the programable clock circuit arrangement 120 having the clock circuit 122, and the programmable time interval unit 124. This arrangement 120 is used to set the times by means of the delay/state-test button 74, when the applications of stimuli, via the lights 70, 72, and/or the speaker 68, are undertaken to help a sleeping person start a lucid dream and/or to continue a lucid dream.

Figure 8:
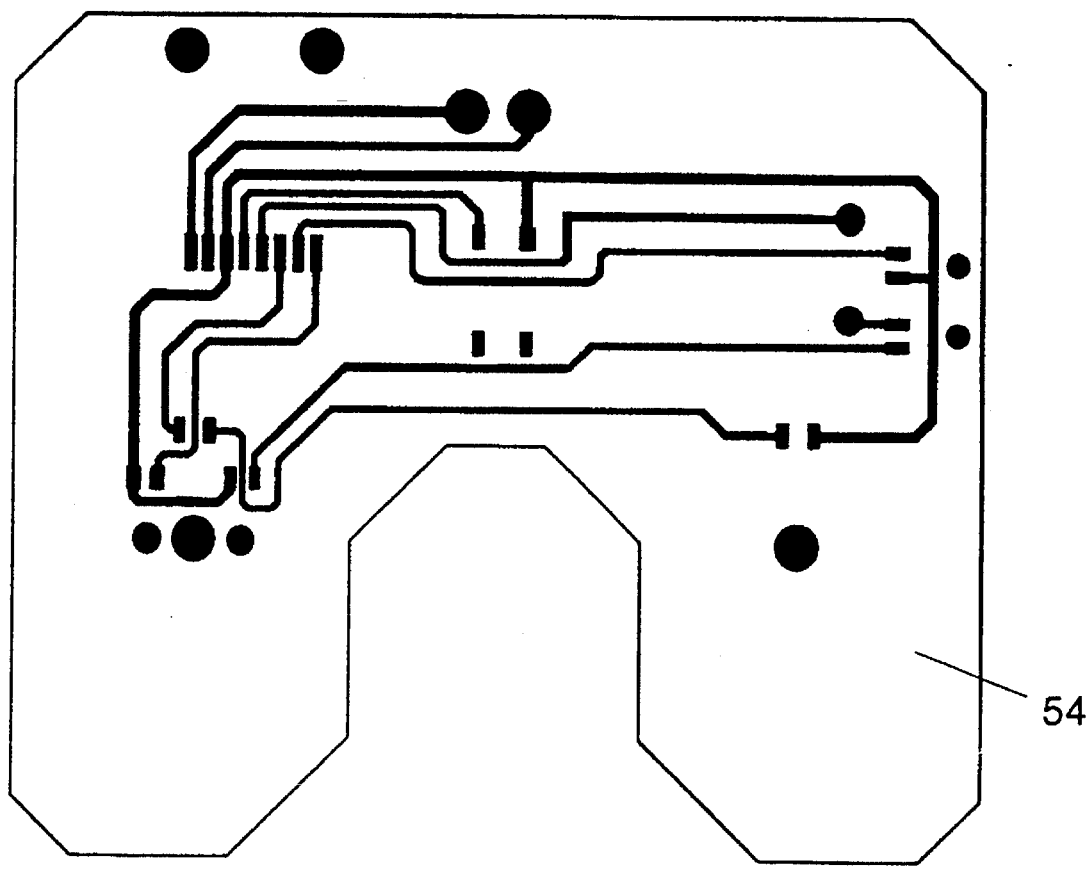
FIG. 8, in respect to the preferred embodiment, illustrates a printed circuit arrangement which is supported in the face mask.
Figure 9A:
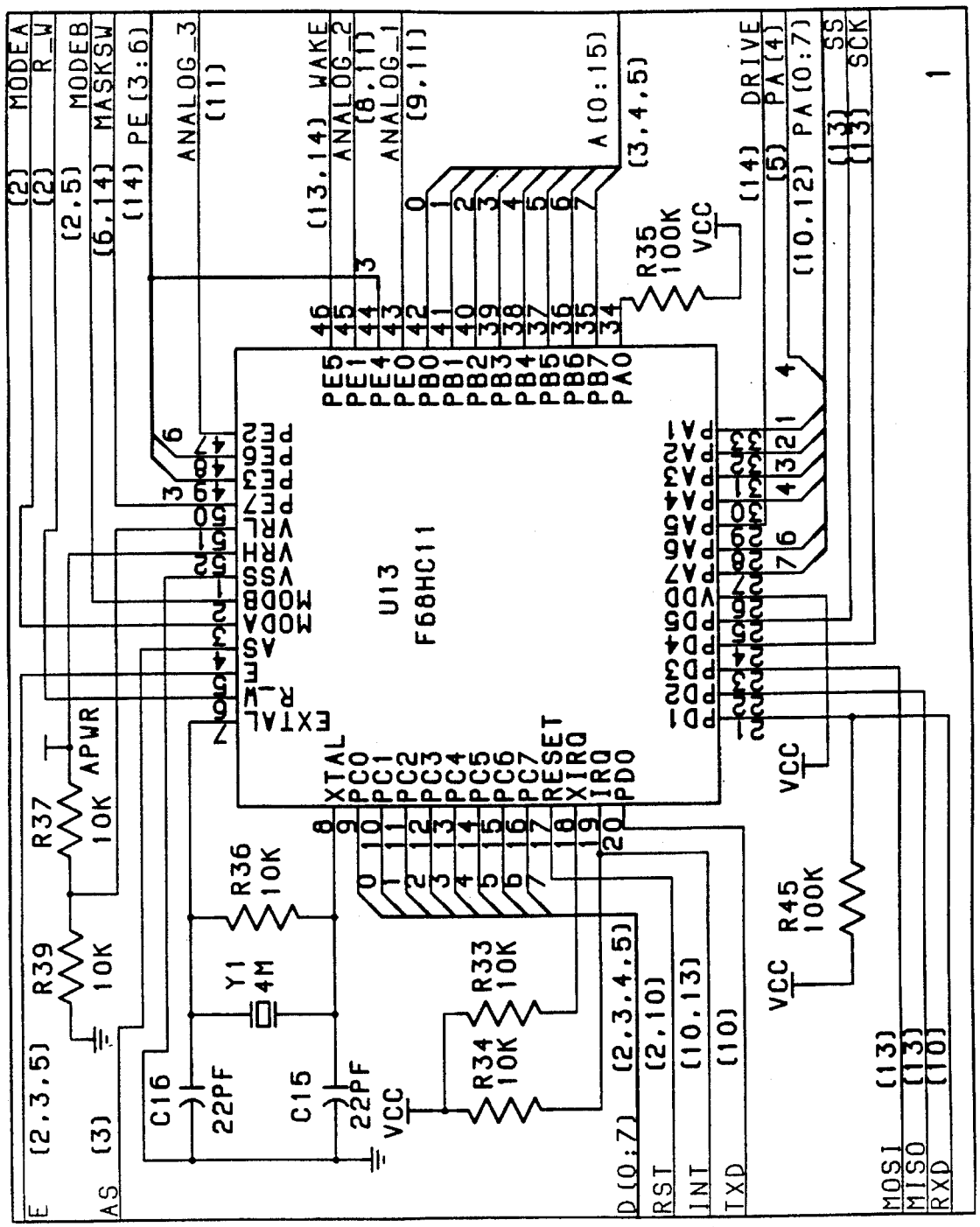
FIGS. 9A–9E, 9J, and 9N illustrate the extensive digital circuitry system of the preferred circuit arrangement of the preferred embodiment.
Figure 9B:
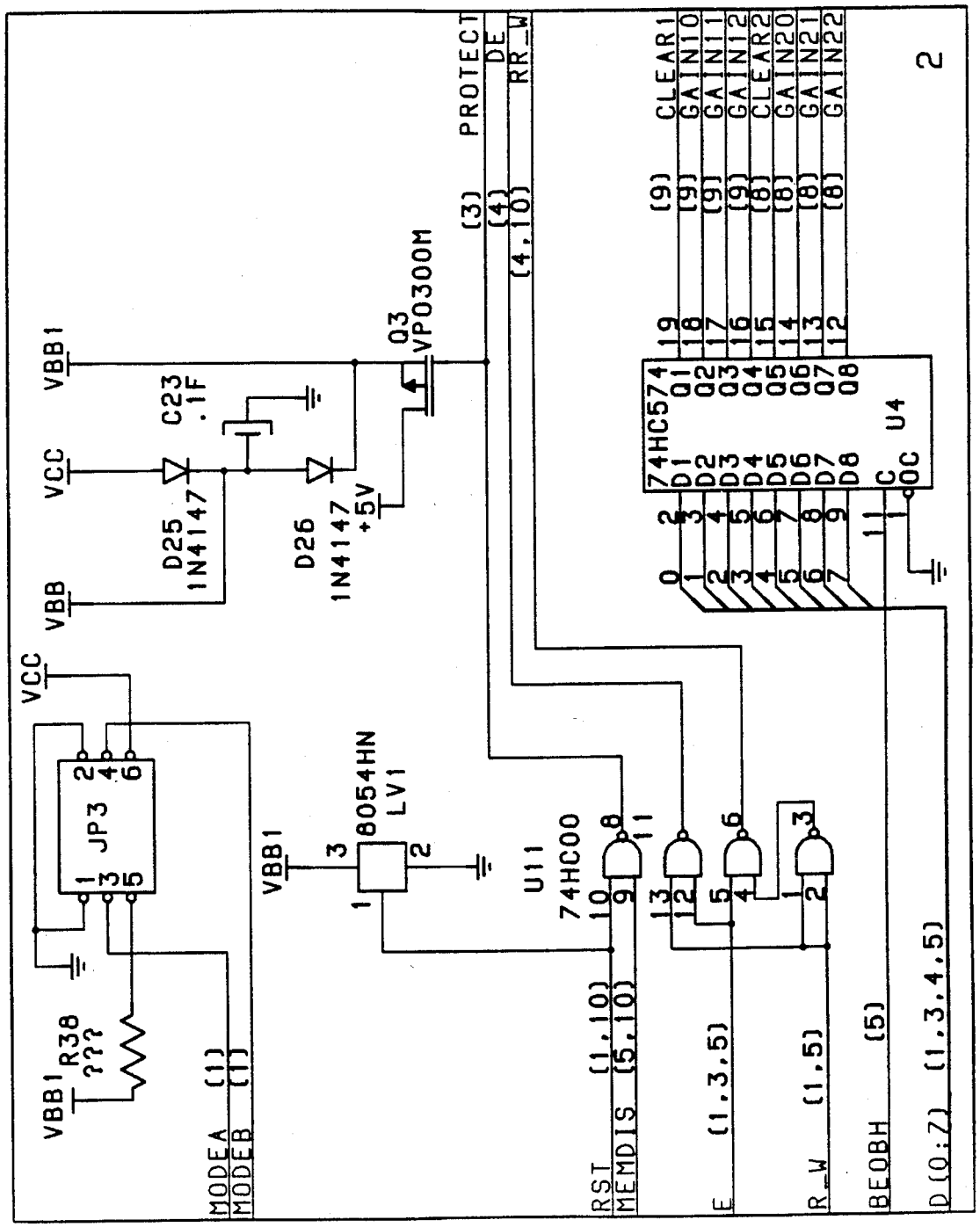
Figure 9C:
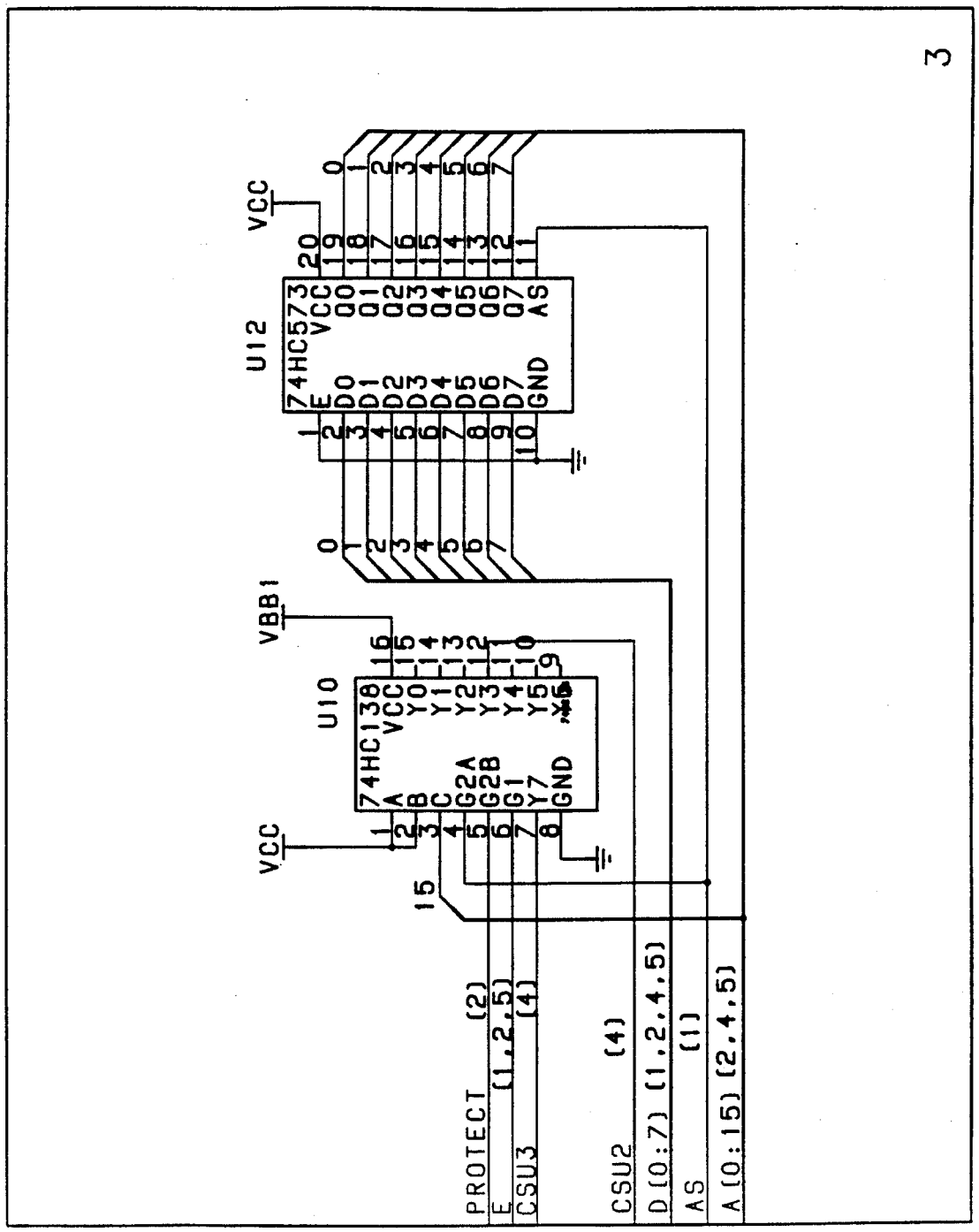
Figure 9D:
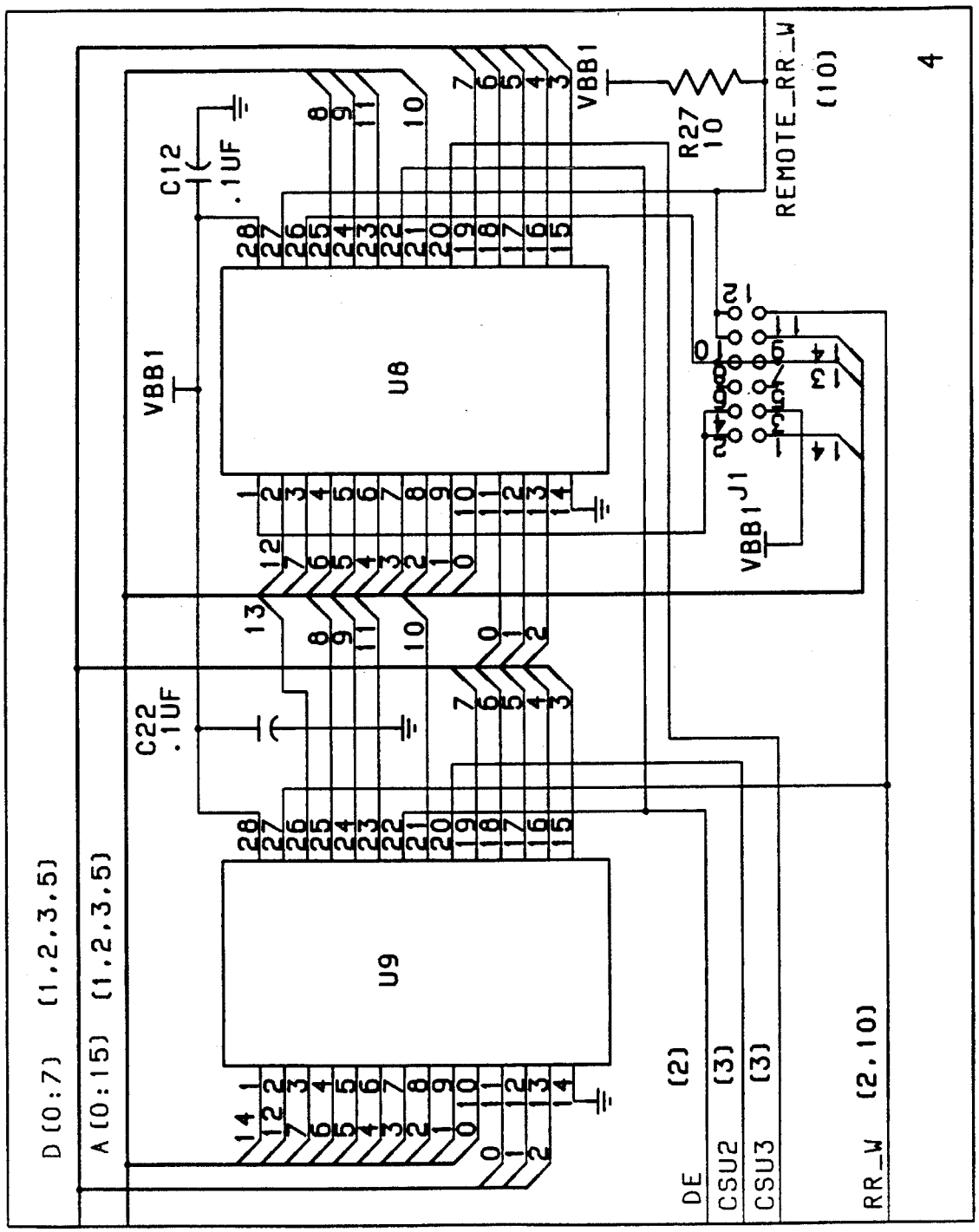
Figure 9E:
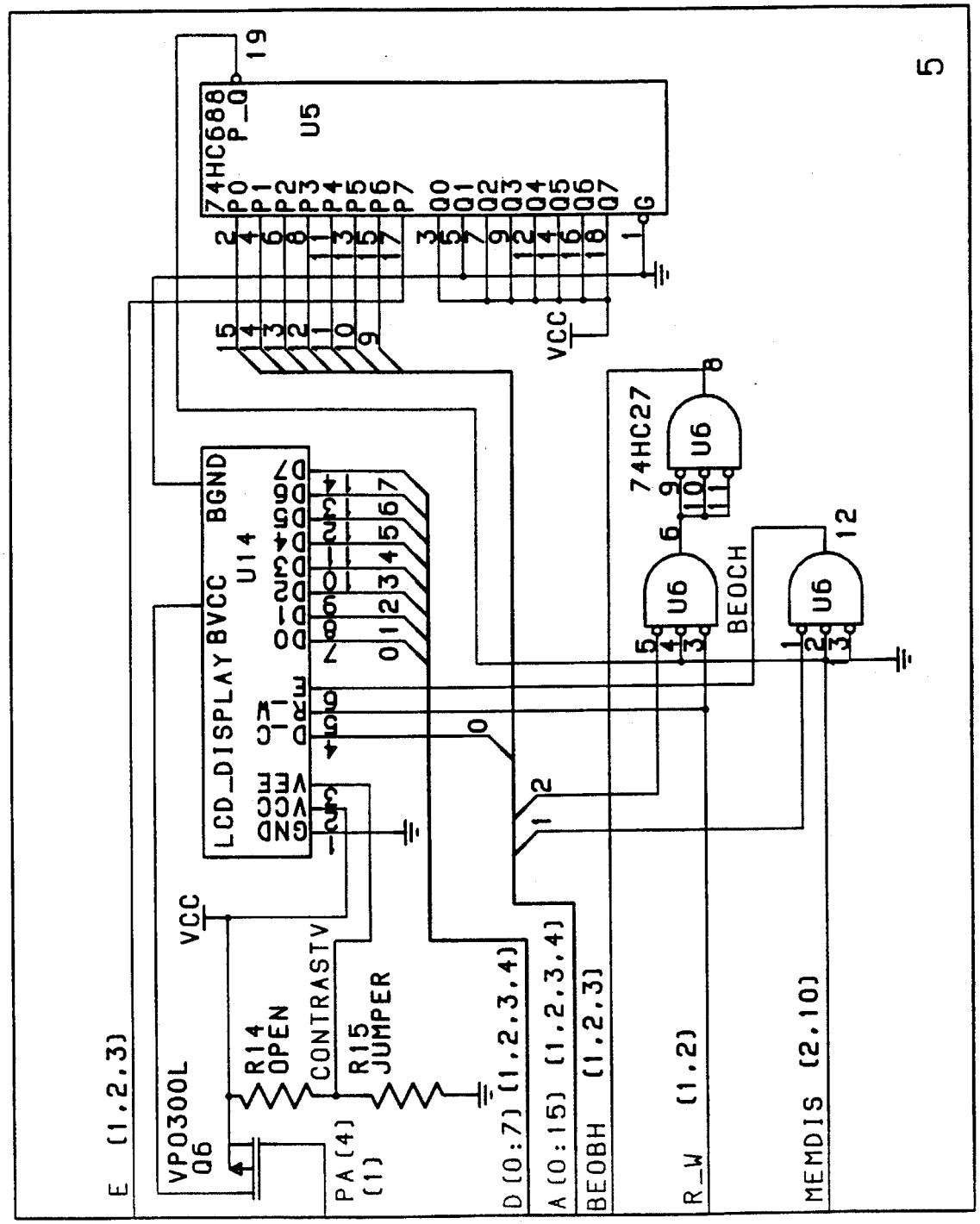
Figure 9F:
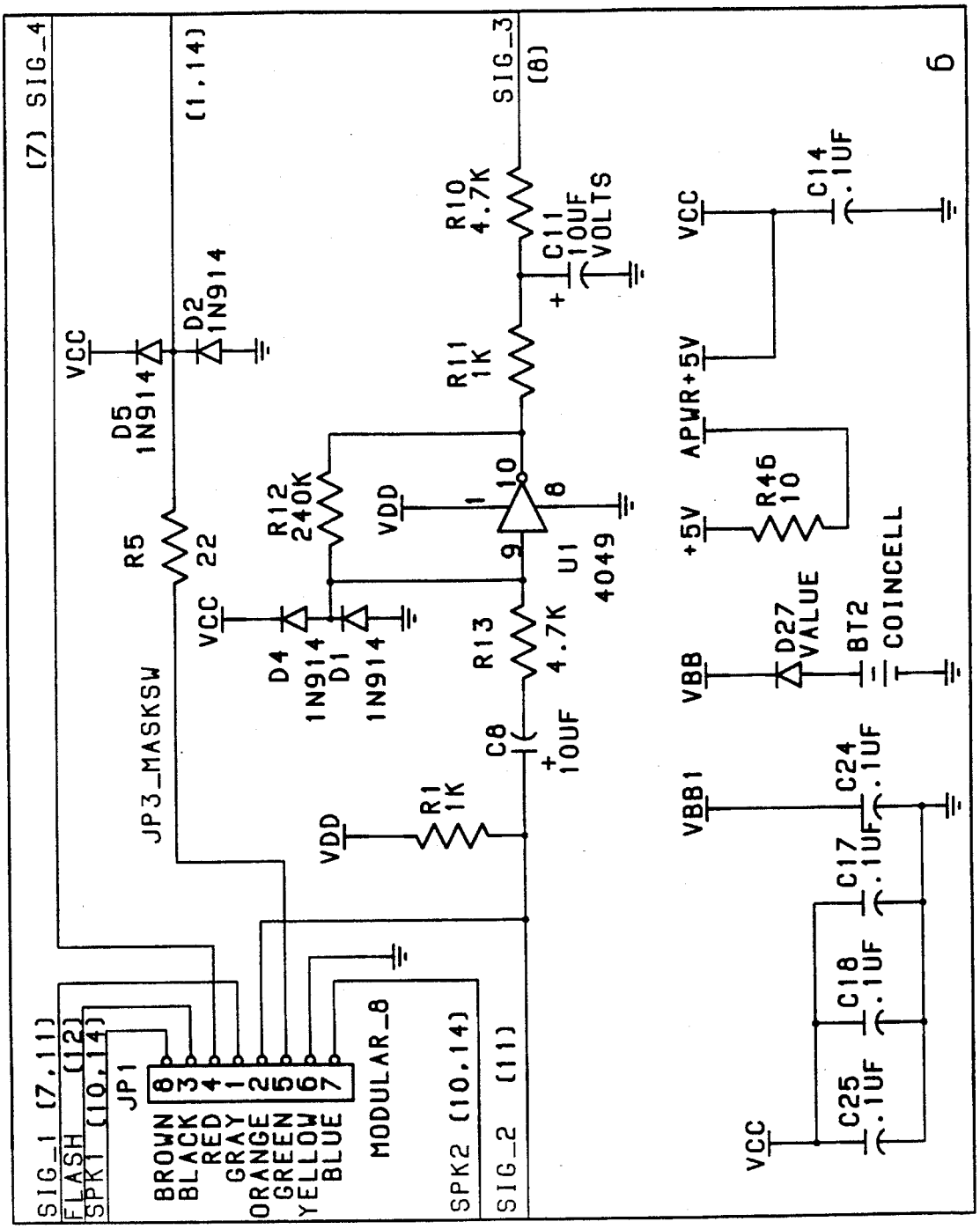
FIGS. 9F–9I illustrate circuitry, which is designated as the integrating mask interface circuitry.
Figure 9G:
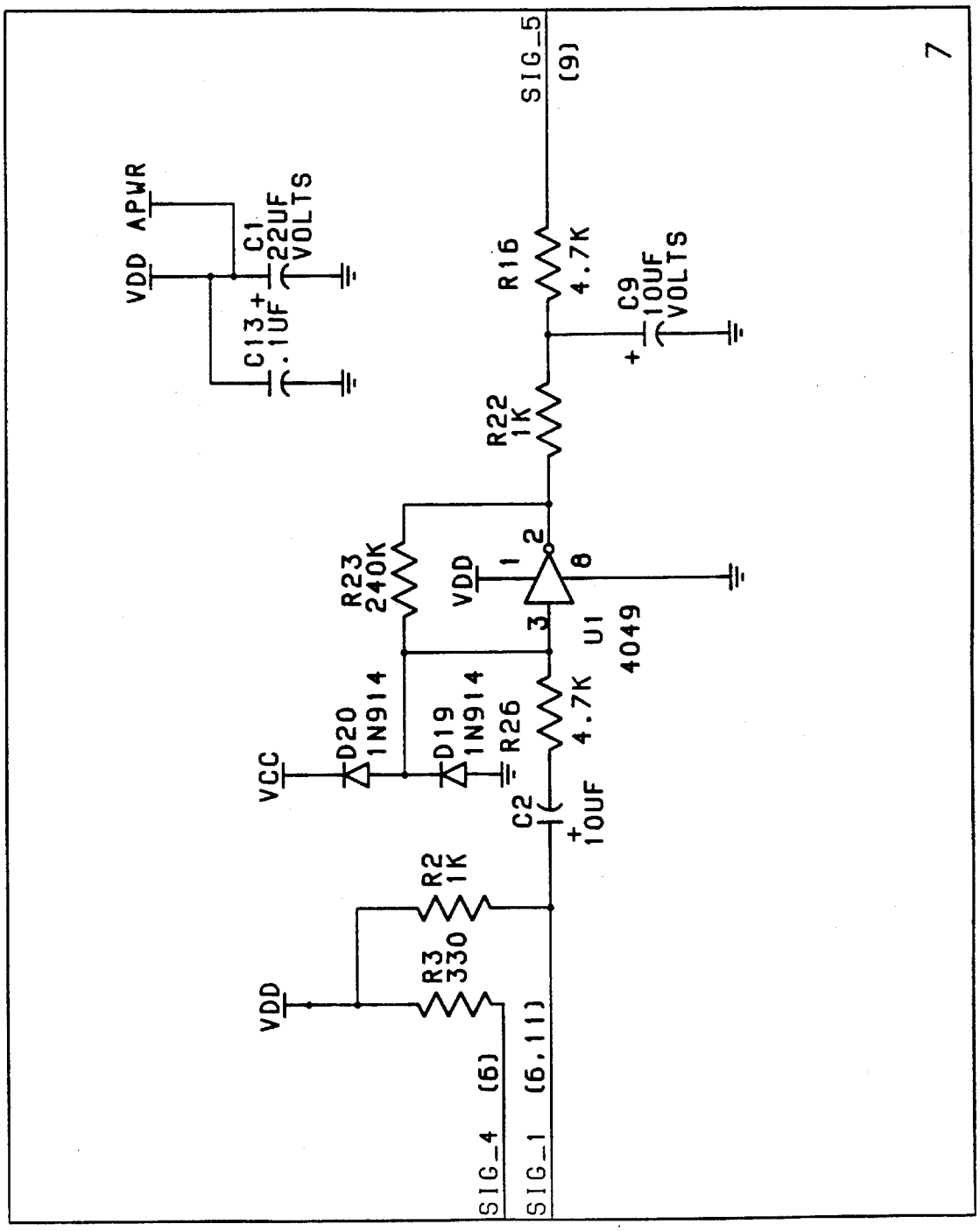
Figure 9H:
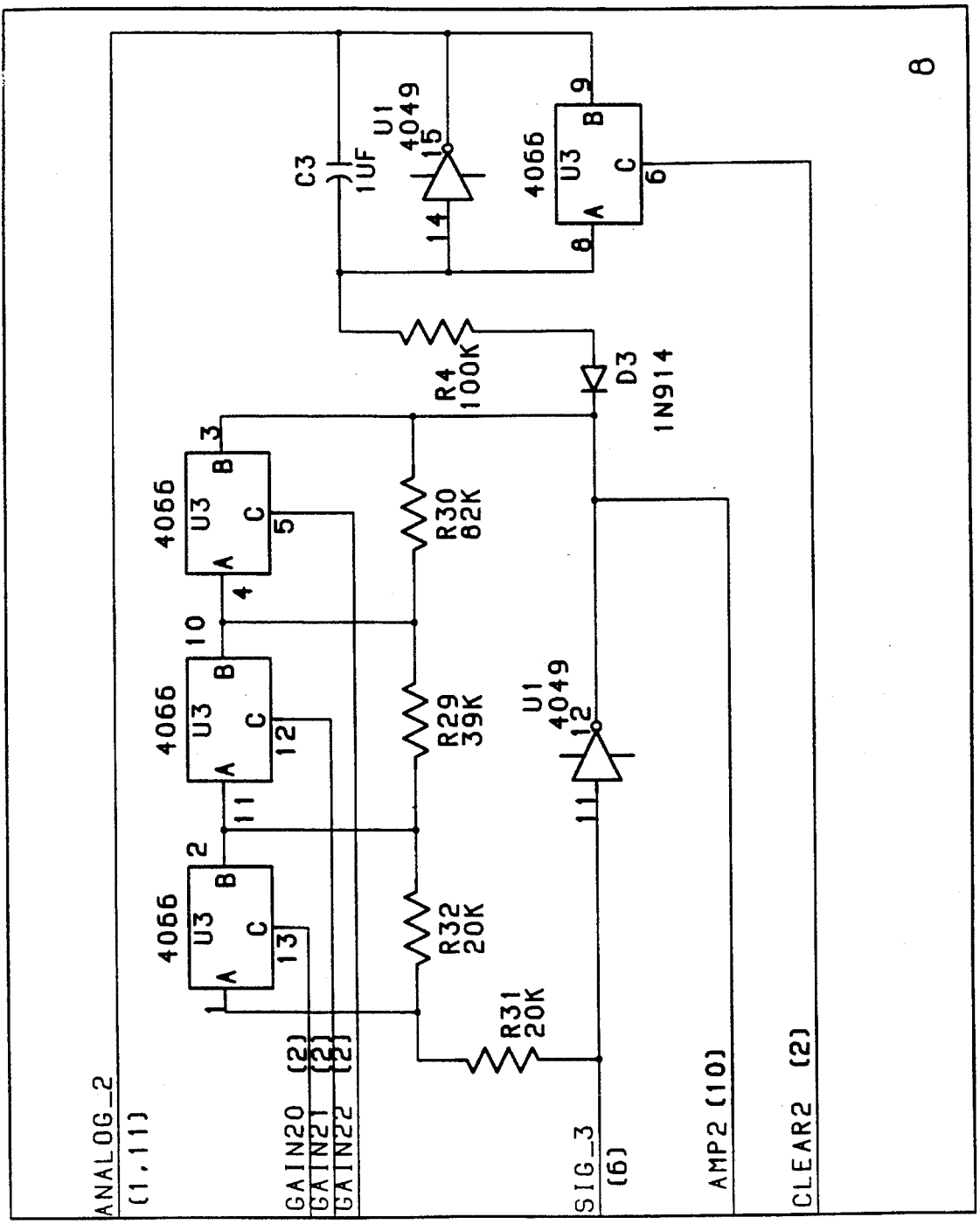
Figure 9I:
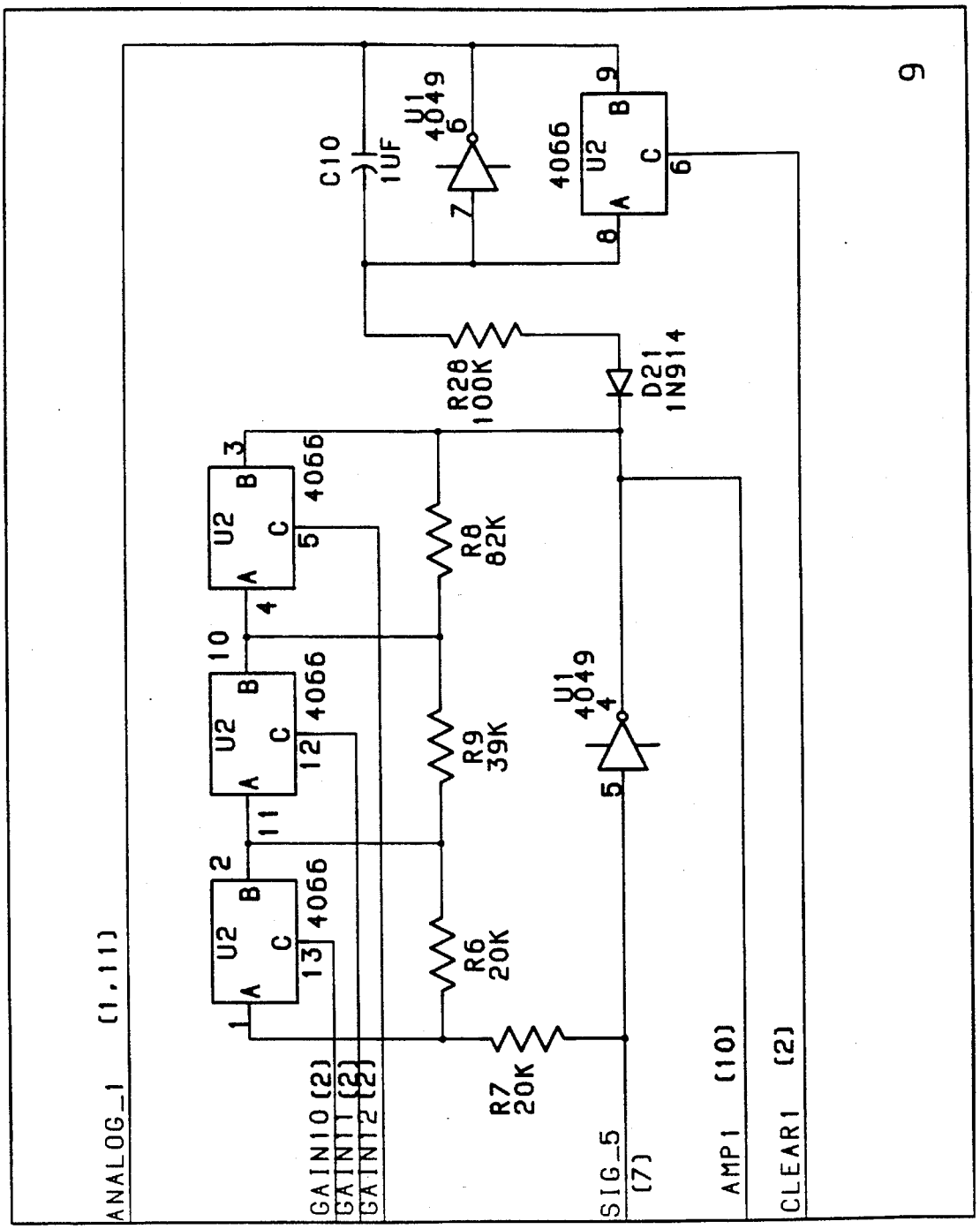
Figure 9J:
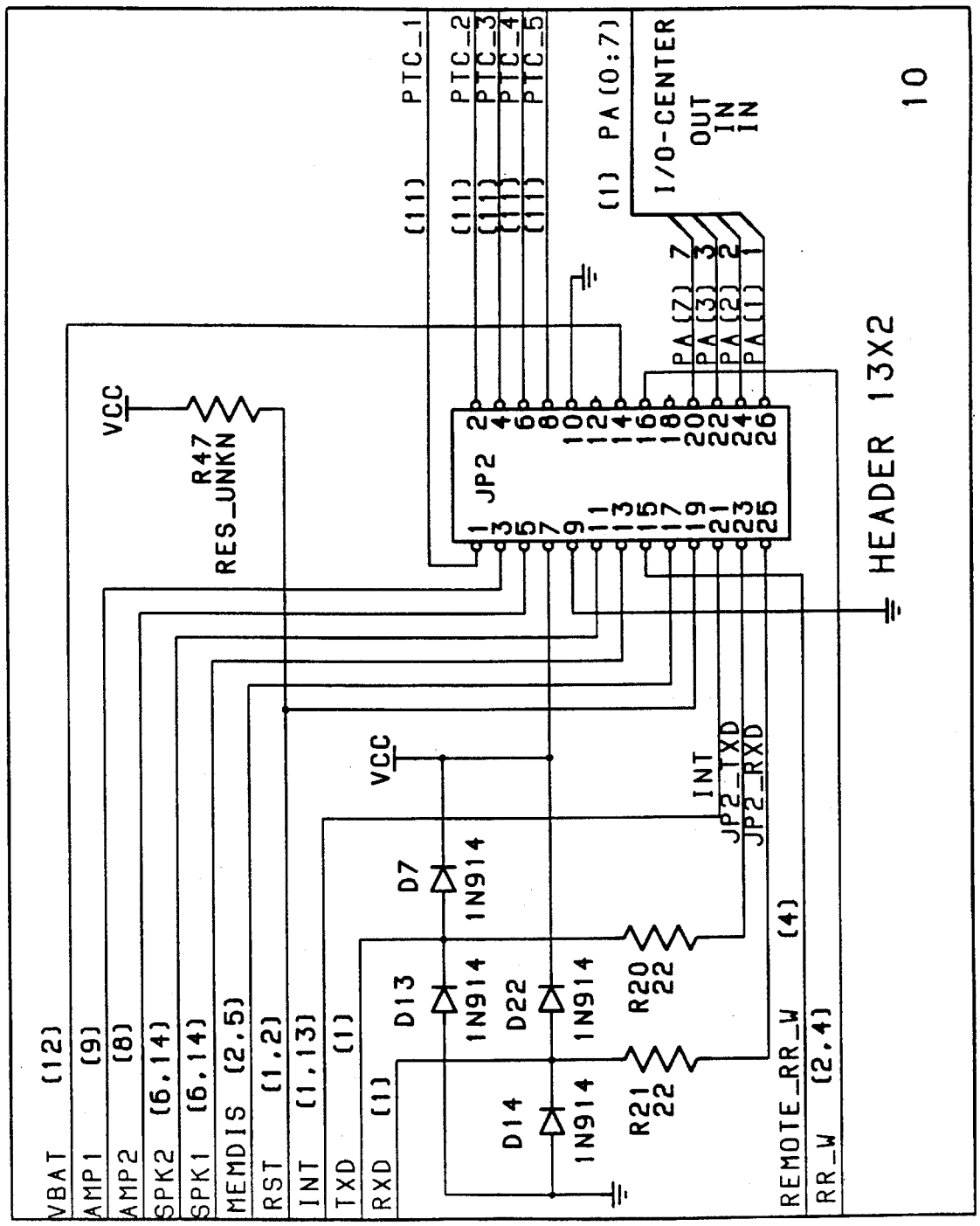
Figure 9K:
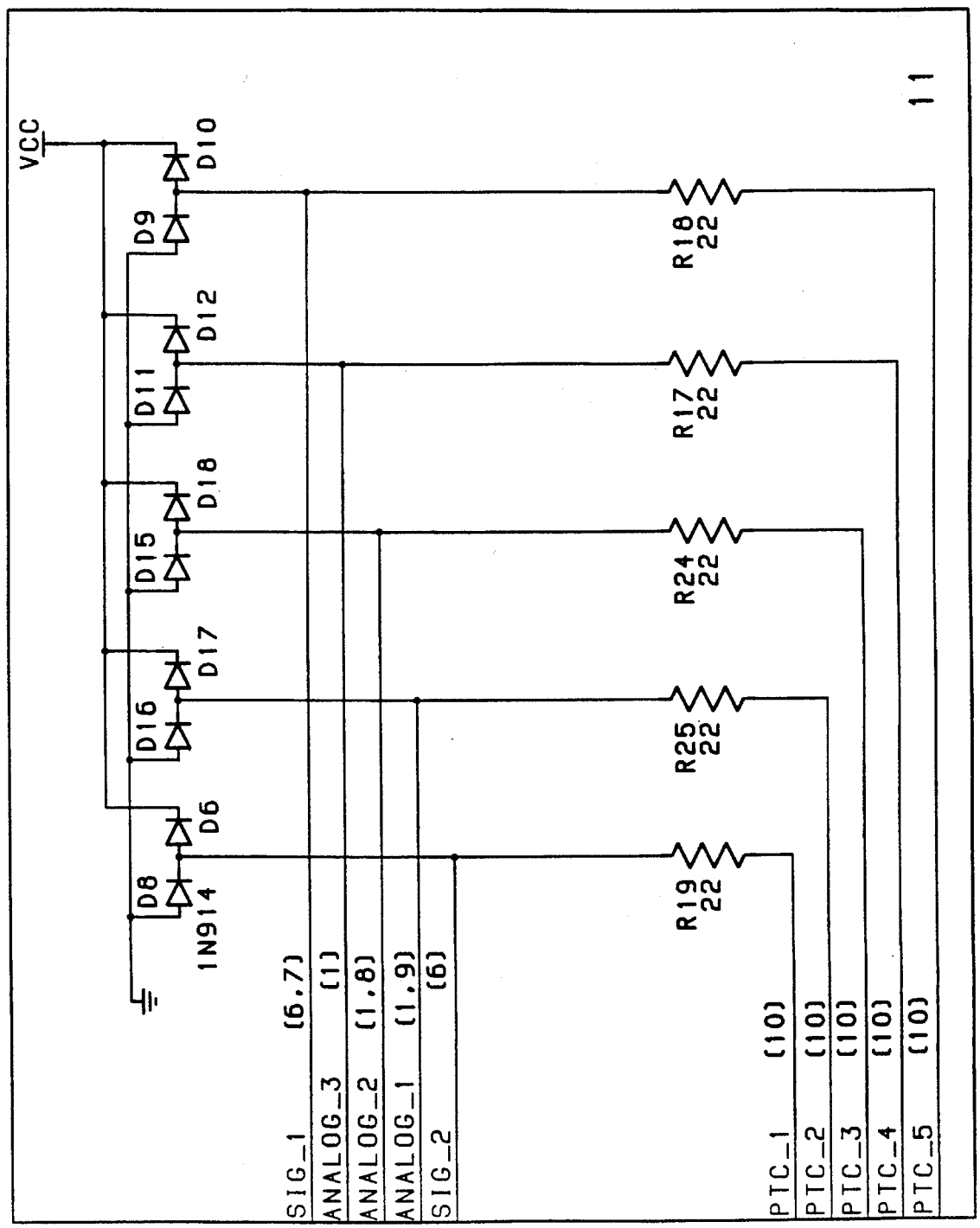
FIGS. 9K and 9L illustrate circuitry, which is designated as the power supply circuitry.
Figure 9L:
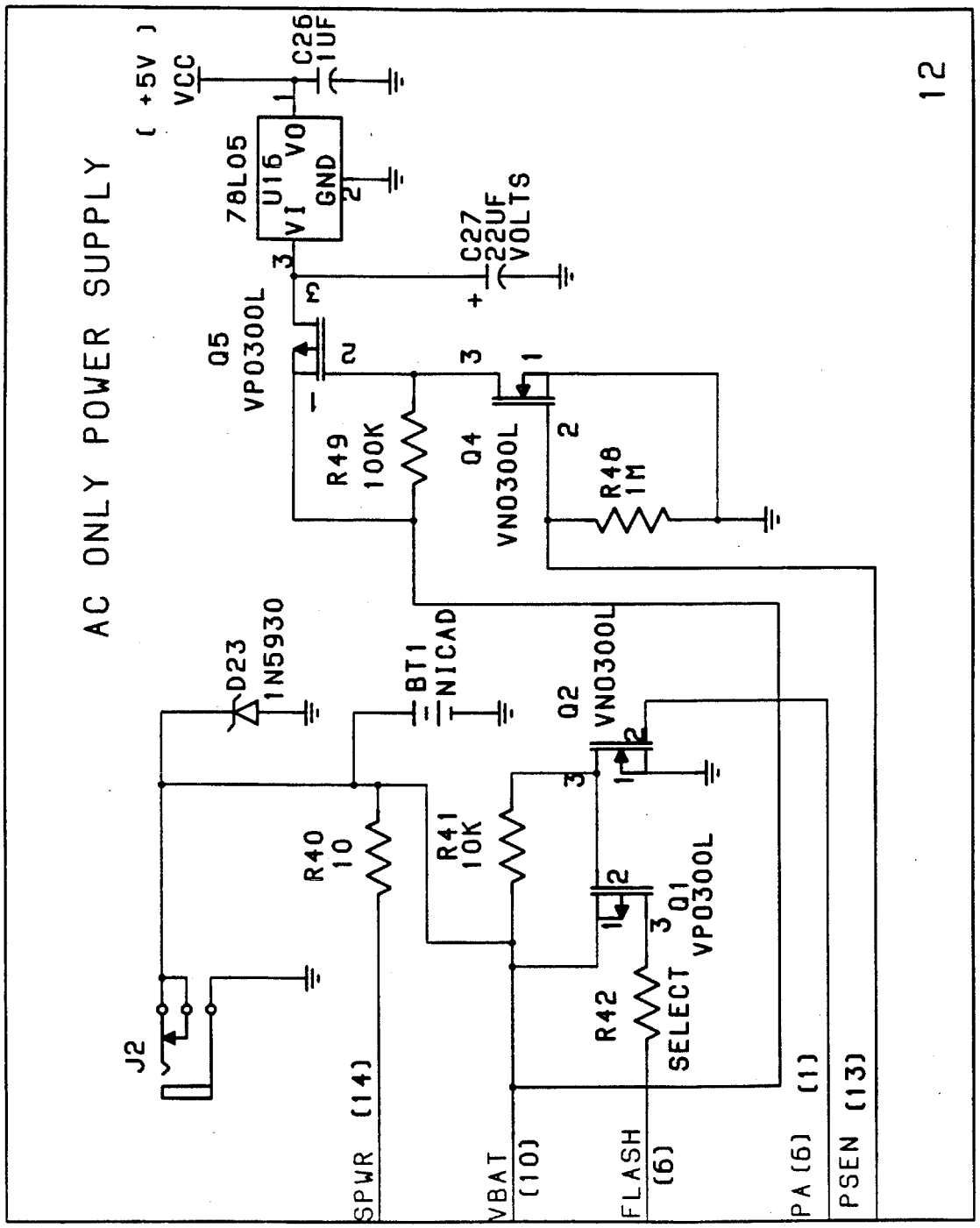
Figure 9M:
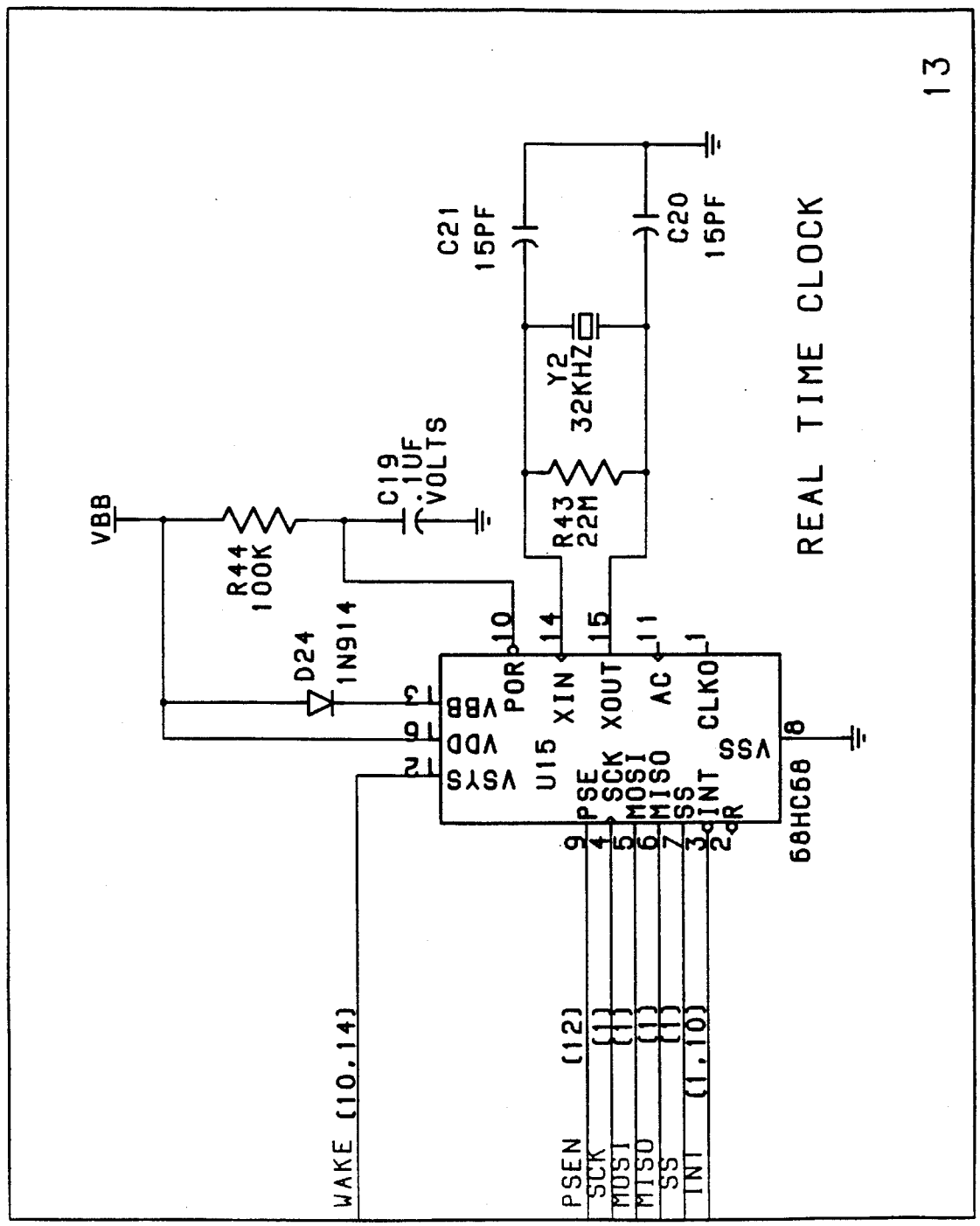
FIG. 9M illustrates circuitry, which is designated as real time clock circuitry.
Figure 9N:
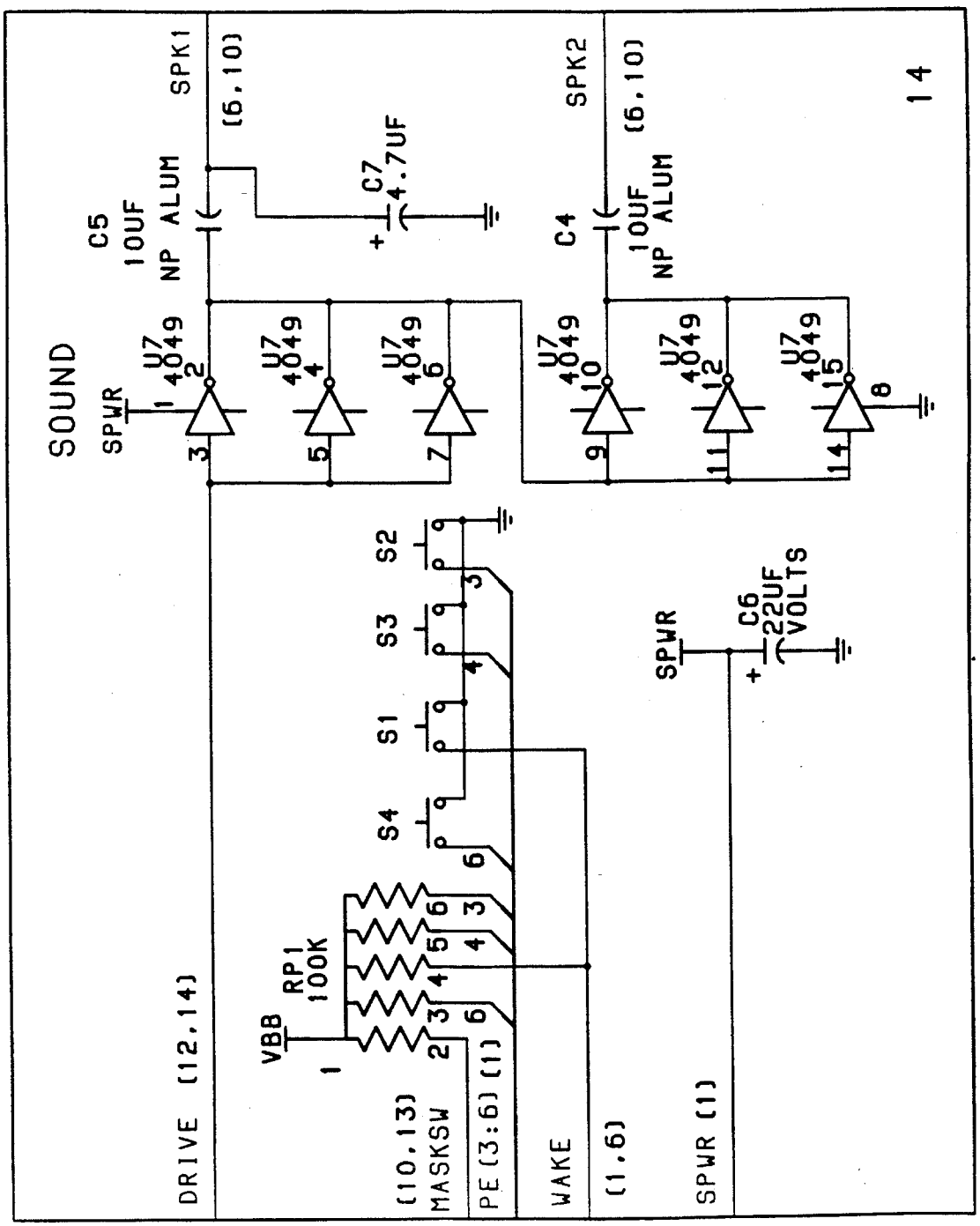

More Specific Information Concerning the Embodiments of the Equipment, in Respect to Selected Preferred Arrangements of the Electrical and Electronic Components In FIGS. 8 through 13, printed circuit boards, also known as PC boards, and also circuit diagrams are shown, which were prepared before translating some of the information of some of their circuitry onto printed circuit boards. FIG. 8 illustrates the PC board 54 of the face mask 34. FIGS. 9a–9n illustrate the digital circuit system 128 of this preferred embodiment of the equipment 30.

Figure 10:
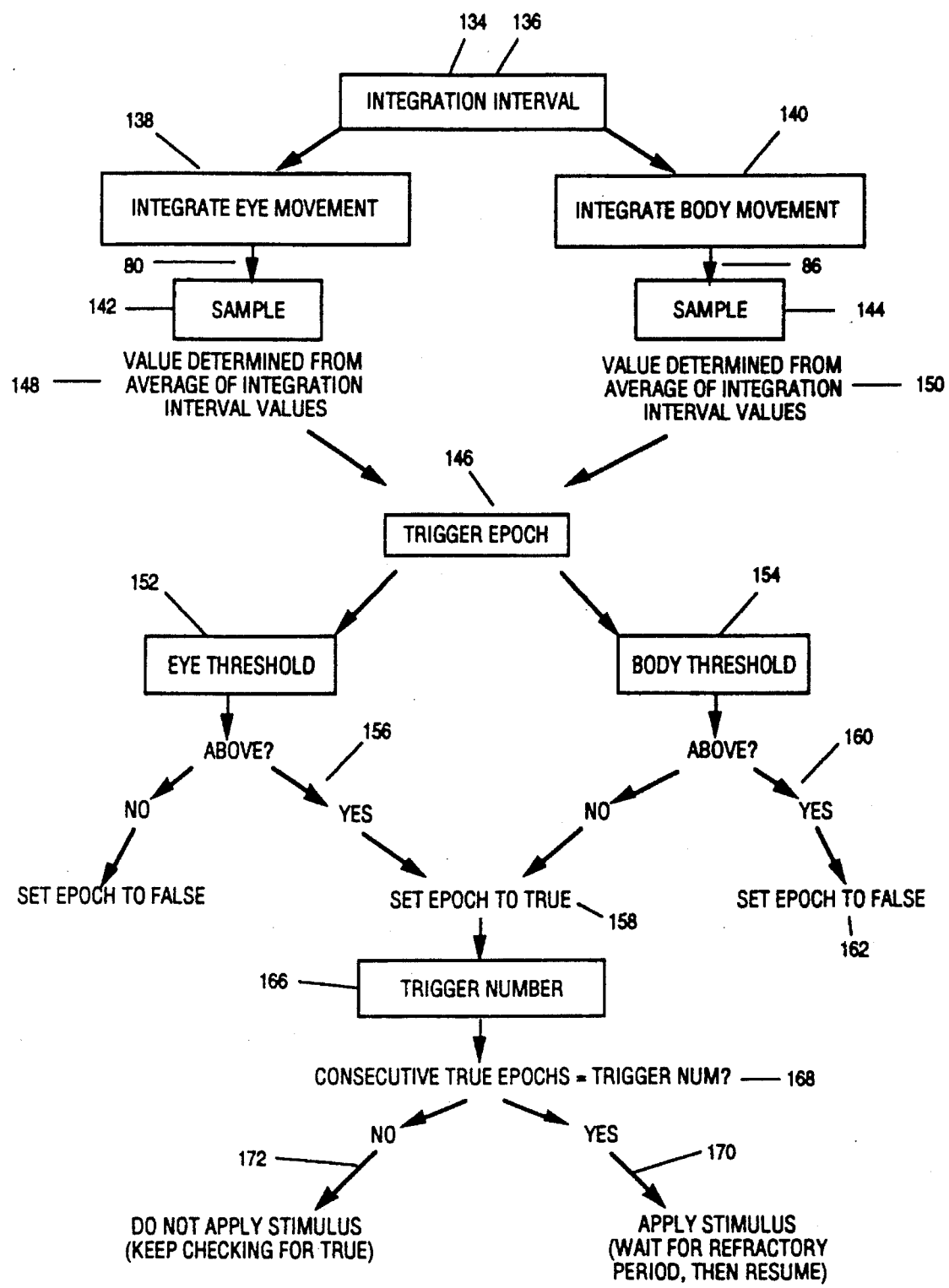
FIG. 10 is a flow chart for the decision making algorithm pertaining to the determination of a person's REM sleep period, and then followed by the determination of when to trigger stimuli only during stable periods of his or her REM sleep.

FIG. 10 presents the circuitry of the programmable clock circuit arrangement 129 and this circuitry is referred to as the real time clock circuitry. FIG. 11 illustrates the power supply circuitry 130, which is part of the overall circuitry 44 of the assembly of the components 40 placed on the table 42, as shown in FIG. 1.

In referring back to FIG. 5 and the integration block 104 of the analog signal conditioning 82, an integrating mask interface circuit 132 is illustrated in FIG. 12. The sound circuitry 133 is presented in FIG. 13.

The Algorithm Pertaining to the Preferred Embodiment

The decision algorithm 134, pertaining to the preferred embodiment, used first in determining when a sleeping person is in a rapid eye movement sleep period, referred to as a REM sleep period, and then in determining when stimuli should be triggered during the sleeping person's stable periods of his or her REM sleep, to cue him or her that he or she is lucidly dreaming, is illustrated in the flowchart presented in FIG. 14. Three hierarchical time periods or intervals are utilized. The shortest time period or hierarchical interval is designated as the Integration Interval 136. During this interval 136, both eye movement signals and body movement signals, illustrated in boxes designated Integrate Eye Movement 138 and Integrate Body Movement 140, are allowed to charge integrating capacitors of the analog signal conditioning circuitry 82, as shown in FIG. 4, or of the integration unit 104, as shown in FIG. 5. This charging occurs before the computer 90 will take a sample 142 of the capacitor voltage reached in the eye movement channel 80, and will also take a sample 144 of the capacitor voltage reached in the body movement channel 86, and thereafter resets the respective integration units 104.

The next longest time period or hierarchical interval is designated as the Trigger Epoch 146. During this interval 146, or next longest time period 146, there are several integration times. In the computer 90, numbers, derived from signals representing eye movement signals or samples 142, and representing body movement signals or samples 144, are respectively averaged over all of the integration times within each trigger epoch 146, arriving at an eye movement channel 80 averaged value 148, and a body movement channel 86 averaged value 150.

These respective averaged values 148, 150, are respectively compared to a user programmable eye threshold 152 and to a user programmable body threshold 154. If the eye movement is above 156 the eye threshold 152, then it has been determined that a sufficient number of eye movements have occurred during that trigger epoch 146 to call it REM sleep or true 158. However, if a sufficient number of body movements create a body average 150 which is above 160, the body threshold 154, during this same trigger epoch 146, then the trigger epoch will be labeled false 162. Only if the body movement average 150 falls below the body threshold 154, will a trigger epoch 146 be labeled true 158.

The third, last, and longest time period or hierarchical interval is designated as the trigger number 166, which determines how many consecutive trigger epochs 166 must be labeled true 168, before a stimulus 170 will be applied. If an insufficient number of consecutive trigger epochs 168 are being labeled true 170, then no, 172, stimulus will be applied.

To paraphrase or summarize the operation of the preferred embodiment 30 of the equipment 30, in respect to the decision algorithm 134 detection flow, as illustrated in the flowchart of FIG. 14, the process comprises: in the integration interval 136, the resolution of a person's eye movement sensing is determined; in the trigger epoch interval 146, whether or not a person's REM sleep is occurring during a specified interval is determined; and then in the trigger number interval 166, how long a wait is to be, during a continuous period of a person's REM sleep, before applying a stimulus, is determined.

A Chart for Software Implementation Pertaining to the Preferred Embodiment

A software chart for software implementation pertaining to the preferred embodiment 30 of the equipment 30, is illustrated in various aspects in FIG. 15. On the front panel of the computer 90 is the display area 180, or screen 180. Lower on the panel and below the display area 180 are the respective finger tip receiving areas 182, also referred to as buttons 182. There are four of them, and in FIG. 15, they appear as follows: the power or mode button 184; the yes or increase button 186; the no or decrease button 188; and the delay or exit button 190; an additional button on the mask. The mask button 74 or mask switch 74 also functions as equivalent to delay or exit button 190.

The sequencing of the finger pressing of the buttons 182 and what will be seen in the display area or screen 180 at the outset is illustrated. If the pressing sequences of the mode finger tip receiving area or button 184 continue, then the edit mode or expert edit mode are reached, showing how various functions are commenced and terminated, as further described via the printed information on these figures.

Continuing Comments Regarding the Operation of the Preferred Embodiments

Continuing the information presented in FIG. 11 regarding the operation of the preferred embodiment, this equipment 30 is operated in two basic modes, sense and edit. The normal operating mode will sense eye movements, give stimuli, and provide a variable delay before stimuli can be applied. In this mode, the delay/state-test button can be pressed at any time to increment the delay in ten minute steps. The alphanumeric display will show delay time while in this mode. The second mode is edit mode, where the equipment 30 stops monitoring eye movements and provides access to the edit parameters. The edit mode is accessed by pressing the mode button once. Each successive press of the mode button will step through the list of adjustable parameters. The increment and decrement buttons will change the values of the parameters in this list. To exit edit mode, press the delay button. Or, if no buttons have been pressed for thirty seconds, the equipment 30 will automatically revert to normal operation.

Pressing YES button 186 and NO button 188 at the same time will manually trigger the stimulus. Regardless of which button was pressed first, the equipment 30 should revert to the mode it was in before either was pressed. This will allow the user to check the stimulus parameters while in edit mode without having to return to the parameter being edited.

While in sense mode, every press of the delay button will add ten minutes to the delay time before the equipment 30 starts sensing eye movements. The delay button will not add to the delay time in one instance: if it is pressed in order to exit edit mode.

The delay/state-test button causes a flash and beep each time it is pressed while in sense mode. This light and sound stimulus provides a convenient state-test to inform users in case they have experienced a so-called "false-awakening." If they are only dreaming that they are pressing the button, it is likely that no flash/sound stimulus will occur, in accordance with the observation that dreamed machines seldom work correctly. This provides an immediate and automatic indication to users that they are probably dreaming, thereby inducing a lucid dream. While counting a delay, the display shows the time remaining before operation begins. This display provides a rough real-time countdown to operating time, but may switch off to save batteries after a specified wait. When actually operating in sense mode, the display could read sensing. After a specified interval, the display will blank out to preserve batteries.

Any time mode is pressed, the delay time will be reset to zero minutes. When pressing mode from normal operating mode, the first item in the list below beep will appear. Each successive press of mode will step through the list of items, which will loop around when the end is reached. When not pressed for thirty seconds, or when delay is pressed from edit mode, the equipment 30 will revert to normal operation.

The pressing of beep on or off, controls whether or not the equipment 30 will beep with every threshold crossing detected. This should not affect beeps used to tell the person operating the equipment 30 that a button has been pressed, especially the delay button.

The flash length of the light stimuli, by changes of one second, is undertaken throughout a range of one to ninety nine seconds. Likewise the flash brightness is changeable in increments from one to ninety nine percent. Although these increments are referred to as brightness changes, actually the pulse widths of the stimuli flashes are being changed. The flash rate is also changed in increment steps from one to ninety nine. In addition, both window counts and window lengths are respectively changed in increments from one to ninety nine.

When using this preferred embodiment 30, the person helping another person, who is trying to lucidly dream or is lucidly dreaming, operates the equipment 30 to be sure the sleeping person's eye movement signals are carefully processed and analyzed to accurately determine the presence of REM sleep. The stimulus, light and/or sound, is applied at the best time during the person's REM sleep. The stimulus applied is strong enough to be perceivable during a person's REM sleep, but not be so strong as to awaken the sleeping person. Ideally, the overall stimuli should incorporate into the dreams of the sleeping person in a clear and recognizable way.

In respect to the equipment 116, the fewer components will be programmed by the person before he or she intends to fall asleep. The delay/state-test button 74 operates in exactly the same way as it does in the preferred embodiment 30, incrementing the countdown timer 120 by 10 minutes with every button press and also providing the convenient state-test as described previously. Thereafter, the programmable clock circuit arrangement 120 controls the timing of the lights 70, 72, and/or the speaker 68.

Specific Information Regarding Some Components of the Preferred Embodiment

The equipment 30 has two bright light emitting diodes 70, 72 referred to as LEDs serving as the light stimuli. Their duration, pulse width, and brightness are adjustable. The color red is used in this lighting but other colors could be used. Incandescent lights could be used. The sound stimuli is created by a small speaker, also referred to as a bone-conductance transducer, mounted on the face mask to be positioned against the forehead of the sleeping person. The sound created consists of short clicks, and their pitch and frequency are adjustable.

The face mask 34, as shown in FIGS. 1, 3, and 6, is made of a light plastic sheet 78 and light plastic foam 76, which together are held by an elastic cloth strap or headband 56, which encircles the head of the person who will be or is sleeping. The light plastic foam 76 is removable from the light plastic sheet 78 for cleaning the foam material.

The main unit housing 52 of the assembly of components 40, which is placed on the table 42, as shown in FIG. 1, is six inches long, four inches wide, and one inch high. The overall weight of this main unit housing 52, in which the computer electronics are arranged, is one pound. This housing 52 is made of ABS plastic materials, which are molded and machined.

Inside the housing 52, the computer 90 has, in turn, a single chip microprocessor, a battery backed RAM (Random Access Memory), and optionally a ROM(Read Only Memory). Recorded data regarding the sleeping persons dreaming may be uploaded to another computer for storing the sleep information and/or for displaying this sleep information. All the software and hardware is interchangeable, always reaching the objective of helping a person, who is dreaming, to have his or her lucid dreams.

A small plug-in wall transformer provides direct current power to the equipment 30, and also charges a battery for portable use of the equipment 30. There is an automatic sleep mode to protect and preserve the batteries, which preferably are in a ten point eight volt, one half ampere hour, Ni-Cad battery pack. The battery power operates the equipment 30 for several days without charging the batteries.

Various Embodiments of the Equipment

The equipment embodiment 30, and the equipment embodiment 116, as illustrated and described, indicate the wide range of equipment available and to be available to assist a person with respect to his or her efforts to lucidly dream, and/or to have other persons assist them too.

Various Embodiments of the Method

The numbers of steps in any method planned to assist a person with respect to his or her efforts to lucidly dream, and/or also to have others assist them are selectable. There will be persons who have never had a lucid dream that they were consciously aware of, and wish to have one, who may need considerable assistance. If so the method selected and the steps involved could be extensive, and equipment, as presented in the preferred embodiment 30 could be used.

In contrast, there will be persons who have learned how to lucidly dream, and the number of steps in any method planned to assist them will often be few in number, and the equipment as presented in the embodiment 116 may be used.

We claim:

1. Equipment used to provide low level sensory stimuli to a sleeping person so that he or she may become consciously aware that he or she is dreaming, while he or she continues to sleep and dream, thereby having lucid dreams, comprising:

a) a means to detect the eyelid movements of a sleeping person and to create signals of such eyelid movements;
   b) electrical and electronic component means to supply electrical power to the means to detect eyelid movements, and to receive signals from the means to detect eyelid movements, and when these signals reach a designated rate, then conduct electrical power to a low intensity stimuli producing component means; and
   c) a low intensity stimuli producing component means to receive electrical power from the electrical and electronic component means, while a person is dreaming and effectively stimulating this sleeping person; and
   d) a means whereby the intensity of said stimuli producing means is adjusted so that the stimulus, when applied to the sleeping person, is of low enough intensity so that it does not awaken them, yet is high enough to cause them to become consciously aware they are dreaming while they continue to sleep, thereby having lucid dreams.

2. Equipment as claimed in claim 1, comprising in addition, a face mask, adapted to be worn by the sleeping person, and to support and to position the means to detect the eyelid movements of a sleeping person.

3. Equipment, as claimed in claim 2, comprising, in addition, a stimuli producing component supported and positioned on the face mask.

4. Equipment, as claimed in claim 1, wherein the means to detect eyelid movements of a sleeping person, and to create signals of such eyelid movements, comprises an infrared emitter and an infrared detector positioned to detect the eyelid movements of a sleeping person.

5. Equipment, as claimed in claim 4, comprising in addition, a face mask, to be worn by the sleeping person, and to support and to position the infrared emitter and the infrared detector.

6. Equipment, as claimed in claim 5, comprising, in addition, a stimuli producing component supported and positioned on the face mask.

7. Equipment, as claimed in claim 1, comprising in addition, a means to detect movement of a sleeping person's body area, apart from their eye area, and a means to create signals of such body movements and to be electrically connected to the electrical and electronic component means, that then receive signals from the detection of both eyelid movements and body movements, whereby eyelid movements, per se, will be used in conjunction with operating the stimuli producing component means.

8. Equipment, as claimed in claim 4, comprising in addition, a means to detect movement of a sleeping person's body area, apart from their eye area, and a means to create signals of such body movements and to be electrically connected to the electrical and electronic component means, that then receive signals from the detection of both eyelid movements and body movements, whereby eyelid movements, per se, will be used in conjunction with operating the stimuli producing component means.

9. Equipment, as claimed in claim 7, wherein the means to detect movement of a sleeping person's body area, comprises an infrared emitter and an infrared detector.

10. Equipment, as claimed in claim 8, comprising in addition, a face mask to be worn by the sleeping person, and to support and to position the infrared emitter and the infrared detector that detect eyelid movements.

11. Equipment, as claimed in claim 10, wherein the means to detect movement of a sleeping person's body area, comprises an infrared emitter and an infrared detector.

12. Equipment, as claimed in claim 11, wherein the face mask also supports the infrared emitter and the infrared detector which is used to detect the movement of the sleeping person's body area.

13. Equipment used to provide low intensity level sensory stimuli to a sleeping person so that he or she may become consciously aware that he or she is dreaming, while he or she continues to sleep and dream, thereby having lucid dreams, comprising:

a) infrared emitter and detector means positioned to detect the eyelid movements of a sleeping person;
   b) electrical and electronic component means to supply electrical power to the infrared emitter and to receive an electrical signal from the infrared detector means, and thereafter modify this electrical signal into a digital form;
   c) computer means to receive the digital form of the eyelid movement signals;
   d) software means to process such digital exe movement information, and, based upon preset conditions, control the operation and intensity of a low intensity level stimulus producing component means; and
   e) a low intensity stimuli producing component means located adjacent the sleeping person and arranged to receive energy to create stimuli as determined by the operation of the computer means, when the sleeping person is dreaming, whereby the created stimuli provide the sleeping person with a cue, without awakening her or him, that she or he is lucidly dreaming.

14. Equipment used to make a sleeping person aware he or she is dreaming, as claimed in claim 13, comprising, in addition, a face mask to be worn by the sleeping person, and to support and to position the infrared emitter and the infrared detector.

15. Equipment, as claimed in claim 14, wherein the face mask also supports and positions the stimuli producing component means.

16. Equipment used to make a sleeping person aware he or she is dreaming, as claimed in claim 13, comprising in addition, another infrared emitter and an infrared detector positioned to detect movement of a body area apart from the eye area of a sleeping person, and also electrically connected to the electrical and electronic component means, the computer means, software and data storage means, to present digital data of such facial area movements to insure the eyelid movement digital data will be truly representative of only eyelid movements.

17. Equipment used to make a sleeping person aware he or she is dreaming, as claimed in claim 16, comprising, in addition, a face mask to be worn by the sleeping person and to support and to position the infrared emitters and the infrared detector, that detect eyelid movements.

18. Equipment, as claimed in claim 17, wherein the face mask also supports and positions the stimuli producing component means.

19. Equipment, as claimed in claim 18, wherein the stimuli producing component means provides a light stimuli.

20. Equipment as claimed in claim 18, wherein the stimuli producing component means provides a sound stimuli.

21. Equipment as claimed in claim 18 wherein the stimuli producing component means provides both a light stimuli and a sound stimuli.

22. Equipment as claimed in claim 21, comprising, in addition, a data storage to receive signal data from the computer.

23. Equipment as claimed in claim 13, comprising, in addition, a data storage to receive signal data from the computer means.

24. A method to assist persons who desire to lucidly dream, to prepare such persons for lucidly dreaming, and then, when such persons are sleeping, at a time when their eye movements become rapid enough for a selected time, to then create a stimuli which they will respond to, without awakening, and thereby they will realize they are lucidly dreaming, comprising the steps of:

a) providing a sleeping place for a person;
 b) observing this sleeping person to determine when her or his eyelid movements are moving rapidly to indicate when her or his eyes are moving quickly enough to determine the person is in a rapid eye movement sleep period;
 c) determining when this sleeping person has been in his or her rapid eye movement sleep period long enough to receive stimuli; and
 d) applying stimuli to this sleeping person without awakening this person.

25. A method, as claimed in claim 24, wherein an initial step is added of counseling a person about lucid dreaming.

26. A method, as claimed in claim 24, wherein a step is added of placing an infrared emitter and an infrared detector nearby the person to create signals indicating the eyelid movements of the sleeping person, which signals are observed, while observing this sleeping person to determine when this sleeping person is in a rapid eye movement sleep period.

27. A method, as claimed in claim 26, wherein a step is added of placing another infrared emitter and an infrared detector nearby the sleeping person to create signals indicating the body movements of the sleeping person, which signals are observed, while observing this sleeping person to determine when this sleeping person is in a rapid eye movement sleep period, whereby these body movement signals are accounted for to thereby realize the eyelid motions, per se.

28. A method, as claimed in claim 26, wherein a step is added of placing a face mask over the face of the person who will be sleeping, and thereafter during the placing of the infrared emitter and the infrared detector, they will be placed on this face mask.

29. A method, as claimed in claim 27, wherein a step is added of placing a face mask over the face of the person who will be sleeping and thereafter during the placing of both infrared emitters and infrared detectors, they will all be placed on this face mask.

30. A method, as claimed in claim 28, wherein a step is added of placing a stimuli producing component on the face mask.

31. A method, as claimed in claim 29, wherein a step is added of placing a stimuli producing component on the face mask.

32. A method, as claimed in claim 28, wherein a step is added of placing a light stimuli producing component on the face mask.

33. A method, as claimed in claim 29, wherein a step is added of placing a light stimuli producing component on the face mask.

34. A method, as claimed in claim 28, wherein a step is added of placing a sound stimuli producing component on the face mask.

35. A method, as claimed in claim 29, wherein a step is added of placing a sound stimuli producing component on the face mask.

36. A method, as claimed in claim 28, wherein a step is added of placing a light and sound producing component on the face mask.

37. A method, as claimed in claim 29, wherein a step is added of placing a light and sound producing component on the face mask.

38. A method, as claimed in claim 26, wherein the step is added of placing electrical and electronic components nearby the sleeping person to supply electrical power to the infrared emitter and to receive an electrical signal from the infrared detector, and thereafter to modify this electrical signal into a digital form.

39. A method, as claimed in claim 38, wherein the step is added of placing a computer to receive the digital form of the eyelid movement signals.

40. A method, as claimed in claim 39, wherein the step is added of providing software means for counting the frequency of occurrence of eyelid movements from the digital form of the eyelid movement signals and, according to preset conditions, causing the timely operation of the stimuli producing component means during the rapid eye movement sleep period of the sleeping person.

* * * * *